United States Patent
Feng et al.

(10) Patent No.: US 11,568,581 B2
(45) Date of Patent: *Jan. 31, 2023

(54) SYSTEMS AND METHODS FOR CORRECTING MISMATCH INDUCED BY RESPIRATORY MOTION IN POSITRON EMISSION TOMOGRAPHY IMAGE RECONSTRUCTION

(71) Applicant: SHANGHAI UNITED IMAGING HEALTHCARE CO., LTD., Shanghai (CN)

(72) Inventors: Tao Feng, Houston, TX (US); Hongdi Li, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 64 days.

This patent is subject to a terminal disclaimer.

(21) Appl. No.: 17/098,463

(22) Filed: Nov. 16, 2020

(65) Prior Publication Data

US 2021/0065412 A1 Mar. 4, 2021

Related U.S. Application Data

(63) Continuation-in-part of application No. 16/695,045, filed on Nov. 25, 2019, now Pat. No. 10,839,567, (Continued)

(51) Int. Cl.
*G06T 11/00* (2006.01)
*A61B 6/00* (2006.01)
(Continued)

(52) U.S. Cl.
CPC .......... *G06T 11/005* (2013.01); *A61B 6/037* (2013.01); *A61B 6/5235* (2013.01);
(Continued)

(58) Field of Classification Search
CPC ......... G06T 11/005; G06T 7/11; G06T 7/174; G06T 7/20; G06T 7/32;
(Continued)

(56) References Cited

U.S. PATENT DOCUMENTS 7,813,783 B2    10/2010   Thomas et al.
2008/0107229 A1  5/2008   Thomas et al.
(Continued)

FOREIGN PATENT DOCUMENTS

CN    106618628 A    5/2017
CN    106691487 A    5/2017
(Continued)

OTHER PUBLICATIONS

First Office Action in Chinese Application No. 201910073990.4 dated Aug. 17, 2020, 21 pages.
(Continued)

*Primary Examiner* — Jose L Couso
(74) *Attorney, Agent, or Firm* — Metis IP LLC

(57) ABSTRACT

The disclosure relates to PET imaging systems and methods. The systems may obtain a plurality of PET images of a subject and a CT image acquired by performing a spiral CT scan on the subject. Each gated PET image may include a plurality of sub-gated PET images. The CT image may include a plurality of sub-CT images each of which corresponds to one of the plurality of sub-gated PET images. The systems may determine a target motion vector field between a target physiological phase and a physiological phase of the CT image based on the plurality of sub-gated PET images and the plurality of sub-CT images. The systems may reconstruct an attenuation corrected PET image corresponding to the target physiological phase based on the target motion vector field, the CT image, and PET data used for the plurality of gated PET images reconstruction.

20 Claims, 16 Drawing Sheets

Related U.S. Application Data which is a continuation of application No. 15/881,765, filed on Jan. 27, 2018, now Pat. No. 10,504,250.

(51) Int. Cl.

| | | |
|---|---|---|
| *G06T 7/11* | (2017.01) | |
| *G06T 7/174* | (2017.01) | |
| *G06T 7/20* | (2017.01) | |
| *G06T 7/32* | (2017.01) | |
| *A61B 6/03* | (2006.01) | |

(52) U.S. Cl.
CPC .......... *A61B 6/5264* (2013.01); *A61B 6/5288* (2013.01); *G06T 7/11* (2017.01); *G06T 7/174* (2017.01); *G06T 7/20* (2013.01); *G06T 7/32* (2017.01); *G06T 2207/10081* (2013.01); *G06T 2207/10088* (2013.01); *G06T 2207/10104* (2013.01); *G06T 2207/30061* (2013.01); *G06T 2211/408* (2013.01); *G06T 2211/421* (2013.01); *G06T 2211/424* (2013.01)

(58) Field of Classification Search
CPC . G06T 2207/10081; G06T 2207/10088; G06T 2207/10104; G06T 2207/30061; G06T 2211/408; G06T 2211/421; G06T 2211/424; G06T 2211/412; G06T 5/001; G06T 5/002; G06T 5/003; G06T 5/007; G06T 5/008; G06T 5/009; G06T 5/50; G06T 7/30; G06T 7/33; G06T 7/0012; G06T 2207/10072; G06T 2207/10076; G06T 2207/10084; G06T 2207/10108; G06T 2207/10112; G06T 2207/30004; G06T 2207/30056; G06T 2207/30064; G06T 2207/10016; G06T 2207/20201; G06T 2207/20221; G06T 2210/41; G06T 2211/40; G06T 2211/416; G06T 2211/428; A61B 6/037; A61B 6/5235; A61B 6/5264; A61B 6/5288; A61B 6/032; A61B 6/4417; A61B 6/469; A61B 6/488; A61B 6/03; A61B 6/541; A61B 6/5258; A61B 5/0816; A61B 5/085; A61B 5/0033; A61B 5/0035; A61B 5/0073; A61B 5/0522; A61B 5/0536; A61B 5/055; A61B 5/0813; A61B 5/113; A61B 5/7292; A61B 8/13; A61B 2090/3735; A61B 2090/374; A61B 2090/3762; G06K 9/6289; G06K 2209/05; G06V 10/803; G06V 2201/03; Y10S 378/901; G01R 33/481

See application file for complete search history.

(56) References Cited

U.S. PATENT DOCUMENTS

| | | |
|---|---|---|
| 2008/0226149 A1 | 9/2008 | Wischmann et al. |
| 2010/0239134 A1 | 9/2010 | Koehler et al. |
| 2010/0245354 A1 | 9/2010 | Rousso et al. |
| 2012/0051664 A1* | 3/2012 | Gopalakrishnan ...... G06T 5/002 |
| | | 382/294 |
| 2012/0078089 A1 | 3/2012 | Wollenweber et al. |
| 2012/0278055 A1 | 11/2012 | Schweizer et al. |
| 2012/0281897 A1 | 11/2012 | Razifar et al. |
| 2012/0305780 A1* | 12/2012 | Thiruvenkadam ..... A61B 6/037 |
| | | 600/407 |
| 2013/0287278 A1 | 10/2013 | Olivier et al. |
| 2013/0315459 A1 | 11/2013 | Wollenweber et al. |
| 2014/0072194 A1 | 3/2014 | Hansis et al. |
| 2014/0099009 A1 | 4/2014 | Lonn et al. |
| 2014/0119611 A1 | 5/2014 | Prevrhal et al. |
| 2014/0270448 A1 | 9/2014 | Mok et al. |
| 2014/0334702 A1 | 11/2014 | El Fakhri et al. |
| 2015/0117733 A1 | 4/2015 | Manjeshwar et al. |
| 2016/0163095 A1 | 6/2016 | Wollenweber |
| 2017/0079608 A1 | 3/2017 | Hamill |
| 2017/0091963 A1* | 3/2017 | Panin .................. A61B 6/5264 |
| 2017/0355572 A1 | 12/2017 | Fan Jin Quan |
| 2018/0174333 A1 | 6/2018 | Feng et al. |
| 2019/0050990 A1 | 2/2019 | Bang et al. |
| 2019/0101655 A1 | 4/2019 | Wang et al. |

FOREIGN PATENT DOCUMENTS

| | | | |
|---|---|---|---|
| CN | 107346556 | 11/2017 | |
| WO | WO-2012153219 A1 * | 11/2012 | ............ A61B 6/032 |
| WO | WO-2012153262 A1 * | 11/2012 | ........... G06T 11/005 |

OTHER PUBLICATIONS

Wu, Zhifang, The Clinical Value of Respiratory Gated PET/CT in Lung Lesions, China Doctoral Dissertations Full-text Database: Medical Science and Technology Series, 2011, 93 pages.

\* cited by examiner

700

| Obtaining a respiration signal of the subject during the scanning, the respiration signal corresponding to a plurality of respiratory phases of the subject | 710 |

↓

| Gating the PET data into a plurality of bins based on the plurality of respiratory phases of the respiration signal, the plurality of bins corresponding to the plurality of respiratory phases | 720 |

↓

| Reconstructing the gated PET data to obtain the plurality of gated PET images corresponding to the plurality of respiratory phases of the subject | 730 |

Determining, for each of the one or more sub-regions, a candidate reference respiratory phase of the CT image based on the sub-regions and corresponding portions in the plurality of gated PET images ~810

Designating one of candidate reference respiratory phases as the reference respiratory phase that matches of the respiratory phase of the CT image ~820

For each of the plurality of gated PET images, determining a similarity between a sub-region in the CT image and the corresponding portion in the gated PET image ~830

Identifying a highest similarity among the determined similarities ~840

Designate the respiratory phase of the gated PET image with the highest similarity as the candidate reference respiratory phase of the CT image ~850

Segmenting one or more bones surrounding the thoracic and abdominal cavity of the subject ~910

Determining one or more margin points of the one or more bones ~920

Determining the VOI based on the one or more margin points ~930

| Obtaining a plurality of gated PET images of a subject, each of the plurality of gated PET images corresponding to a physiological phase of a plurality of physiological phases of the subject, each of the plurality of gated PET images including a plurality of sub-gated PET images each of which corresponds to one of a plurality of portions of the subject | ~1302 |

| Obtaining a CT image of the subject, the CT image being acquired by performing a spiral CT scan on the subject and including a plurality of sub-CT images each of which corresponds to one of the plurality of portions of the subject | ~1304 |

| Determining a target motion vector field between a target physiological phase among the plurality of physiological phases and a physiological phase of the CT image based on the plurality of sub-gated PET images and the plurality of sub-CT images | ~1306 |

| Reconstructing an attenuation corrected PET image corresponding to the target physiological phase based on the target motion vector field, the CT image, and PET data used for the plurality of gated PET images reconstruction | ~1308 |

FIG. 13

SYSTEMS AND METHODS FOR CORRECTING MISMATCH INDUCED BY RESPIRATORY MOTION IN POSITRON EMISSION TOMOGRAPHY IMAGE RECONSTRUCTION

CROSS-REFERENCE TO RELATED APPLICATIONS

This application is a continuation-in-part of U.S. patent application Ser. No. 16/695,045, filed on Nov. 25, 2019, which is a continuation of U.S. patent application Ser. No. 15/881,765, filed on Jan. 27, 2018, now U.S. Pat. No. 10,504,250, the contents of each of which are hereby incorporated by reference.

TECHNICAL FIELD

The present disclosure generally relates to systems and methods for image processing, and more specifically relates to methods and systems for correcting mismatch induced by respiratory motion in positron emission tomography (PET) image reconstruction.

BACKGROUND

PET is a specialized radiology procedure that generates three-dimensional images of functional processes in a target organ or tissue of a subject. Specifically, in PET studies, biologically active molecules carrying radioactive tracer molecules are first introduced into the subject. The PET system then detects pairs of gamma rays emitted indirectly by the tracer and reconstructs an image of the tracer concentration within the subject by analyzing the detected signals. Because the biologically active molecules used in PET studies are natural substrates of metabolism at the target organ or tissue, PET can evaluate the physiology (functionality) of the target organ or tissue, as well as its biochemical properties. Changes in these properties of the target organ or tissue may provide information for the identification of the onset or progression of a disease before an anatomical change relating to the disease become detectable by other diagnostic tests, such as computed tomography (CT) or magnetic resonance imaging (MRI).

Furthermore, the high sensitivity of PET—in the picomolar range—may allow the detection of small amounts of radio-labeled markers in vivo. PET may be used in conjunction with other diagnostic tests to achieve simultaneous acquisition of both structural and functional information of the subject. Examples include a PET/CT hybrid system, a PET/MR hybrid system.

PET and CT data of a subject may be obtained using a PET/CT hybrid system. The CT data may be applied in the attenuation correction of the PET data. During a scan in the PET/CT system, a subject may undergo respiratory motion. When the scanning is performed for chest or upper abdomen examinations, respiratory motion of the lungs and/or cardiac motion of the heart of the subject may lead to a mismatch between the PET data and the CT data. The mismatch may subsequently cause artifacts in the PET image, which in turn may affect an interpretation of the PET image, or a diagnosis performed on the basis of the PET image. Generally, a CT scan is quick and the CT data may correspond to the same or substantially the same respiratory phase. A PET scan is relatively slow and the PET data may correspond to a plurality of respiratory phases, which may lead to a mismatch between the CT data and the PET data. However, in some CT scans, such as a spiral CT scan, different portions (e.g., slices) of the subject are scanned at different times, and CT data of the different portions of the subject may correspond to different respiratory phases. Moreover, the CT data may be obtained when the subject is in a deep expiration/inspiration phase, which may further lead to a mismatch between the PET data and the CT data. Thus, it is desirable to develop methods and systems for matching the CT data and the PET data to reduce the effect of respiratory and/or cardiac motion of the subject and improve the quality of a PET image reconstructed accordingly.

SUMMARY

In a first aspect of the present disclosure, a method for image processing may be implemented on at least one machine, each of which may have a processor and a storage device. The method may include one or more of the following operations. An anatomical image and PET data of a subject may be obtained. The PET data may be gated into a plurality of bins. The plurality of bins may correspond to a plurality of respiratory phases. A plurality of gated PET images may be reconstructed based on the gated PET data. Each gated PET image of the plurality of gated PET images may correspond to a respiratory phase of the plurality of respiratory phases. A motion vector field corresponding to a target respiratory phase with respect to a reference respiratory phase may be determined based on the plurality of gated PET images and the anatomical image. The reference respiratory phase may be related to the anatomical image. A respiratory phase-matched anatomical image for the target respiratory phase may be obtained by transforming a volume of interest (VOI) in the anatomical image based on the motion vector field corresponding to the target respiratory phase with respect to the reference respiratory phase. An attenuation corrected PET image corresponding to the target respiratory phase may be reconstructed based on the respiratory phase-matched anatomical image and the gated PET data.

In some embodiments, the PET data may include a first portion and a second portion. The first portion may be affected more by a respiratory motion of the subject than the second portion. The first portion may correspond to the VOI in the anatomical image.

In some embodiments, the determining a motion vector field corresponding to a target respiratory phase with respect to a reference respiratory phase may include one or more of the following operations. The reference respiratory phase that matches a respiratory phase of the anatomical image may be identified among the plurality of respiratory phases based on the plurality of gated PET images. The motion vector field corresponding to the target respiratory phase may be determined based on a gated PET image corresponding to the target respiratory phase and a reference gated PET image corresponding to the reference respiratory phase.

In some embodiments, the identifying the reference respiratory phase that matches the respiratory phase of the anatomical image may include one or more of the following operations. One or more sub-regions in the anatomical image may be identified. The one or more sub-regions may correspond to at least a portion of a lung and a portion of a liver of the subject. The reference respiratory phase that matches the respiratory phase of the anatomical image may be determined among the plurality of the respiratory phases based on the identified one or more sub-regions in the anatomical image and one or more corresponding portions in each gated PET image of the plurality of gated PET images.

In some embodiments, the one or more sub-regions include a first sub-region and a second sub-region. The identifying one or more sub-regions in the anatomical image may include one or more of the following operations. A left lung and a right lung of the subject in the anatomical image may be segmented. The first sub-region may be determined based on the left lung. The second sub-region may be determined based on the right lung.

In some embodiments, the determining the reference respiratory phase that matches the respiratory phase of the anatomical image may include one or more of the following operations. For each of the identified one or more sub-regions of the anatomical image, a candidate reference respiratory phase may be determined based on the sub-region of the anatomical image and corresponding portions in the plurality of gated PET images. One candidate reference respiratory phase may be designated from the candidate reference respiratory phases as the reference respiratory phase that matches the respiratory phase of the anatomical image.

In some embodiments, for a sub-region in the anatomical image, the determining a candidate reference respiratory phase of the anatomical image may include one or more of the following operations. For each of the plurality of gated PET images, a similarity between the sub-region in the anatomical image and the corresponding portion in the gated PET image may be determined. A highest similarity among the determined similarities may be identified. The respiratory phase of the gated PET image with the highest similarity may be designated as the candidate reference respiratory phase of the anatomical image.

In some embodiments, the determining a similarity between the sub-region in the anatomical image and the corresponding portion in the gated PET image may be based on at least one of pixel-based similarity, entropy-based similarity, mutual information similarity, or contour-based similarity.

In some embodiments, the motion vector field corresponding to a target respiratory phase may be determined by registering the gated PET image corresponding to the target respiratory phase with the reference gated PET image corresponding to the reference respiratory phase.

In some embodiments, the gated PET image with the reference gated PET image may be registered based on at least one of an optical flow registration algorithm, a demons registration algorithm, or a B-spline registration algorithm.

In some embodiments, the segmenting the VOI in the anatomical image may include one or more of the following operations. In the anatomical image, one or more bones surrounding the thoracic and abdominal cavity of the subject located within the scanning region may be segmented. One or more edge points of the one or more bones may be determined. The VOI may be determined based on the one or more edge points.

In some embodiments, the method may further include one or more of the following operations. For each respiratory phase, a motion vector field corresponding to the respiratory phase may be determined by an image registration. For each respiratory phase, a respiratory phase-matched anatomical image may be obtained by transforming the VOI in the anatomical image to generate a corrected anatomical image corresponding to the respiratory phase based on the corresponding motion vector field. For each respiratory phase, an attenuation corrected PET image corresponding to the respiratory phase may be reconstructed based on the corresponding corrected anatomical image and the gated PET data.

In some embodiments, the anatomical image may be at least one of a computed tomography (CT) image or a magnetic resonance (MR) image.

In some embodiments, the PET data may be acquired by a PET scanner with a PET field of view (FOV). The obtaining of the PET data may include acquiring the PET data by locating the at least a portion of the lung and a portion of the liver of the subject in a central region of the PET FOV of the PET scanner.

In a second aspect of the present disclosure, a system may include at least one processor and at least one storage medium for storing instructions. When executing the instructions, the at least one processor may be directed to perform a method including one or more of the following operations. An anatomical image and PET data of a subject may be obtained. The PET data may be gated into a plurality of bins. The plurality of bins may correspond to a plurality of respiratory phases. A plurality of gated PET images may be reconstructed based on the gated PET data. Each gated PET image of the plurality of gated PET images may correspond to a respiratory phase of the plurality of respiratory phases. A motion vector field corresponding to a target respiratory phase with respect to a reference respiratory phase may be determined based on the plurality of gated PET images and the anatomical image. The reference respiratory phase may be related to the anatomical image. A respiratory phase-matched anatomical image for the target respiratory phase may be obtained by transforming a VOI in the anatomical image based on the motion vector field corresponding to the target respiratory phase with respect to the reference respiratory phase. An attenuation corrected PET image corresponding to the target respiratory phase may be reconstructed based on the respiratory phase-matched anatomical image and the gated PET data.

In a third aspect of the present disclosure, a non-transitory computer-readable storage medium may store instructions that, when executed by at least one processor of a system, cause the system to perform a method including one or more of the following operations. An anatomical image and PET data of a subject may be obtained. The PET data may be gated into a plurality of bins. The plurality of bins may correspond to a plurality of respiratory phases. A plurality of gated PET images may be reconstructed based on the gated PET data. Each gated PET image of the plurality of gated PET images may correspond to a respiratory phase of the plurality of respiratory phases. A motion vector field corresponding to a target respiratory phase with respect to a reference respiratory phase may be determined based on the plurality of gated PET images and the anatomical image. The reference respiratory phase may be related to the anatomical image. A respiratory phase-matched anatomical image for the target respiratory phase may be obtained by transforming a VOI in the anatomical image based on the motion vector field corresponding to the target respiratory phase with respect to the reference respiratory phase. An attenuation corrected PET image corresponding to the target respiratory phase may be reconstructed based on the respiratory phase-matched anatomical image and the gated PET data.

In a fourth aspect of the present disclosure, a system may include at least one processor and storage. The system may include an acquisition module and a processing module. The acquisition module may be directed to obtain an anatomical image and PET data of a subject. The processing module may include a gating unit, a reconstruction unit, a motion vector field determination unit, and a transformation unit. The gating unit may be directed to gate the PET data into a plurality of bins, the plurality of bins corresponding to a plurality of respiratory phases. The reconstruction unit may be directed to reconstruct, based on the gated PET data, a plurality of gated PET images. Each gated PET image of the plurality of gated PET images may correspond to a respiratory phase of the plurality of respiratory phases. The motion vector field determination unit may be directed to determine, based on the plurality of gated PET images and the anatomical image, a motion vector field corresponding to a target respiratory phase with respect to a reference respiratory phase relating to the anatomical image. The transformation unit may be directed to obtain a respiratory phase-matched anatomical image for the target respiratory phase by transforming a VOI in the anatomical image based on the motion vector field corresponding to the target respiratory phase with respect to the reference respiratory phase. The reconstruction unit may be further directed to reconstruct, based on the respiratory phase-matched anatomical image and the gated PET data, an attenuation corrected PET image corresponding to the target respiratory phase.

In a fifth aspect of the present disclosure, a system may include at least one processor and at least one storage device for storing instructions. When executing the instructions, the at least one processor may be directed to perform a method including one or more of the following operations. A plurality of gated positron emission tomography (PET) images of a subject may be obtained. Each of the plurality of gated PET images may correspond to one physiological phase of a plurality of physiological phases of the subject. Each of the plurality of gated PET images may include a plurality of sub-gated PET images each of which corresponds to one of a plurality of portions of the subject. A computed tomography (CT) image of the subject may be obtained. The CT image may be acquired by performing a spiral CT scan on the subject and include a plurality of sub-CT images each of which corresponds to one of the plurality of portions of the subject. A target motion vector field between a target physiological phase among the plurality of physiological phases and a physiological phase of the CT image may be determined based on the plurality of sub-gated PET images and the plurality of sub-CT images. An attenuation corrected PET image corresponding to the target physiological phase may be reconstructed based on the target motion vector field, the CT image, and PET data used for the plurality of gated PET images reconstruction.

In some embodiments, the determining a target motion vector field between a target physiological phase among the plurality of physiological phases and a physiological phase of the CT image based on the plurality of sub-gated PET images and the plurality of sub-CT images may include one or more of the following operations. For each of the plurality of sub-CT images, a reference physiological phase of the sub-CT image may be determined among the plurality of physiological phases based on the plurality of sub-gated PET images of the plurality of gated PET images. A motion vector field between the target physiological phase and the reference physiological phase of the sub-CT image may be determined. The target motion vector field between the target physiological phase and the physiological phase of the CT image may be determined based on the motion vector field corresponding to each of the plurality of sub-CT images. The physiological phase of the CT image may include the reference physiological phase of each of the plurality of sub-CT images.

In some embodiments, for each of the plurality of sub-CT images, the determining, among the plurality of physiological phases, a reference physiological phase of the sub-CT image based on the plurality of sub-gated PET images of the plurality of gated PET images may include one or more of the following operations. A plurality of candidate sub-gated PET images that correspond to the same portion of the subject as the sub-CT image may be selected from the plurality of sub-gated PET images of the plurality of gated PET images. For each of the plurality of candidate sub-gated PET images, a similarity degree between the sub-CT image and the candidate sub-gated PET image may be determined. A reference sub-gated PET image that has the highest similarity degree to the sub-CT image may be determined among the plurality of candidate sub-gated PET images. The physiological phase of the reference sub-gated PET image may be designated as the reference physiological phase of the sub-CT image.

In some embodiments, for each of the plurality of candidate sub-gated PET images, the determining a similarity degree between the sub-CT image and the candidate sub-gated PET image may include one or more of the following operations. A first volume of interest (VOI) from the candidate sub-gated PET image may be segmented. A second VOI from the sub-CT image may be segmented. The similarity degree between the sub-CT image and the candidate sub-gated PET image may be determined based on the first VOI and the second VOI.

In some embodiments, the at least one processor may be further configured to direct the system to perform one or more of the following operations. The CT image may be divided into the plurality of sub-CT images each of which corresponds to one of the plurality of portions of the subject. For each of the plurality of gated PET images, the gated PET image may be divided into the plurality of sub-gated PET images each of which corresponds to one of the plurality of portions of the subject.

In some embodiments, the target physiological phase may be an end-inspiration phase.

In some embodiments, the plurality of physiological phases may be respiratory phases. The plurality of respiratory phases may comprise an end-expiration phase, an end-inspiration phase, a deep expiration phase, a deep inspiration phase, and one or more middle respiratory phases between the end-expiration phase and the end-inspiration phase.

In some embodiments, the obtaining a plurality of gated PET images of a subject may include one or more of the following operations. A first gated PET image corresponding to the end-inspiration phase and a second gated PET image corresponding to the end-expiration phase may be determined. A first motion vector field between the end-inspiration phase and the end-expiration phase may be determined based on the first gated PET image and the second gated PET image. For each of the plurality of respiratory phases other than the end-inspiration phase and the end-expiration phase, a second motion vector field between the end-inspiration phase and the respiratory phase may be determined based on the first motion vector field. The gated PET image corresponding to the respiratory phase may be generated based on the second motion vector field and the first gated PET image.

In some embodiments, the obtaining a plurality of gated PET images of a subject may include one or more of the following operations. PET data of the subject acquired when the subject is in a breathing status may be obtained. A first gated PET image corresponding to the end-inspiration phase, a second gated PET image corresponding to the end-expiration phase, and one or more gated PET images corresponding to the one or more middle respiratory phases may be reconstructed based on the PET data. A gated PET image corresponding to the deep expiration phase and a gated PET image corresponding to the deep inspiration phase may be generated based on the first gated PET image and the second gated PET image.

In some embodiments, the at least one processor may be further configured to direct the system to divide the subject into the plurality of portions along a direction perpendicular to an axial plane of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 7 is a flowchart illustrating an exemplary process for gating PET data according to some embodiments of the present disclosure;

FIG. 8A is a flowchart illustrating an exemplary process for determining a reference respiratory phase of a CT image according to some embodiments of the present disclosure;

FIG. 8B is a flowchart illustrating an exemplary process for determining a candidate reference respiratory phase of a CT image according to some embodiments of the present disclosure;

FIG. 9 is a flowchart illustrating an exemplary process for determining a volume of interest (VOI) in a CT image according to some embodiments of the present disclosure;

FIG. 13 is a flowchart illustrating an exemplary process for reconstructing an attenuation corrected PET image corresponding to a target physiological phase according to some embodiments of the present disclosure;

DETAILED DESCRIPTION

Figure 1:
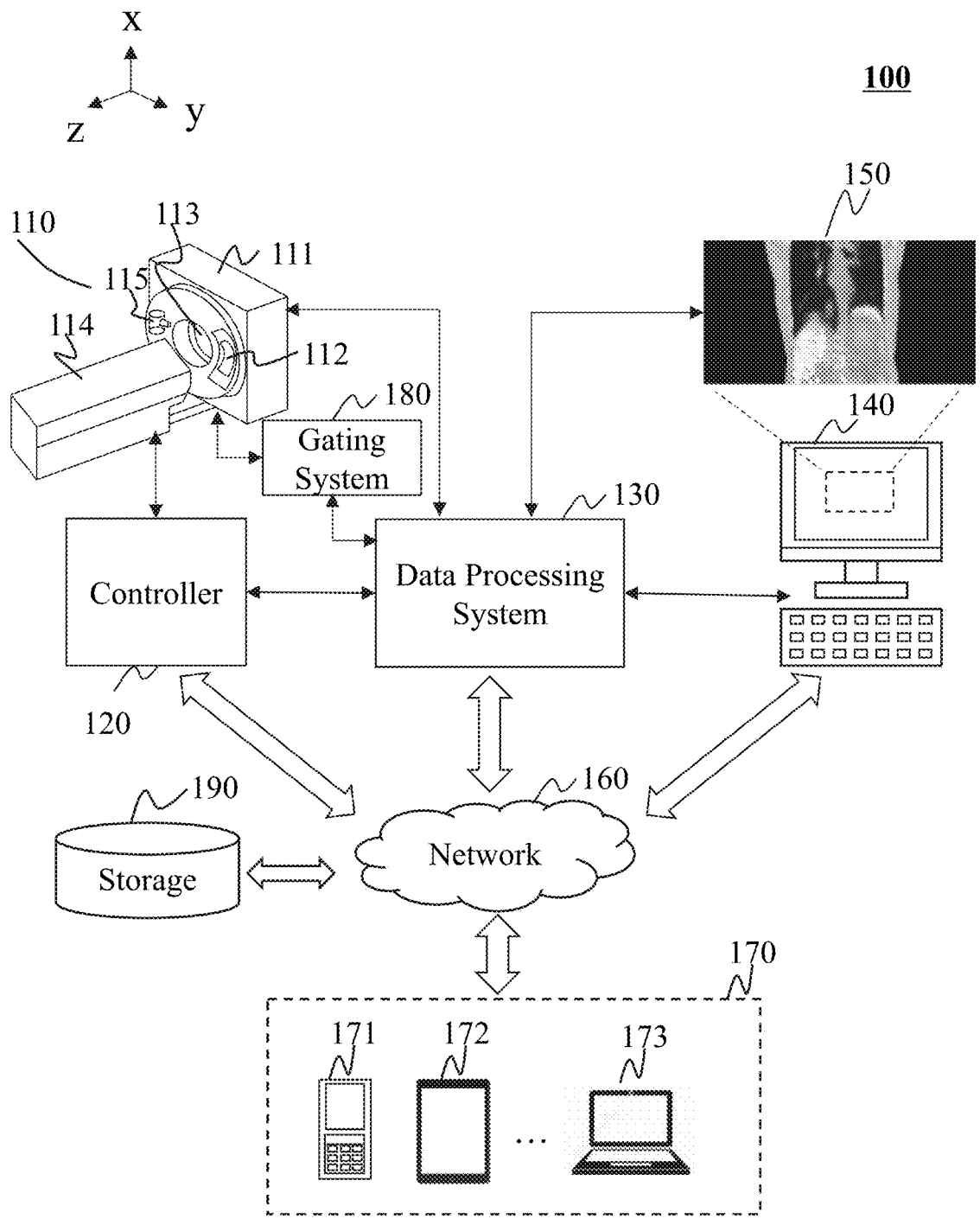
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks, or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, a magnetic resonance imaging (MRI) system, a positron emission tomography (PET) system, a PET-CT system, a PET-MRI system, or the like, or any combination thereof.

The following description is provided to help better understanding of PET/CT image reconstruction methods and/or systems. The term "image" used in this disclosure may refer to a 2D image, a 3D image, a 4D image, and/or any related image data (e.g., CT data, projection data corresponding to the CT data). The term "segment an organ" (e.g., a lung, the liver of a subject) used in this disclosure may refer to segment a portion of an image corresponding to the organ. This is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

The present disclosure relates to systems and methods for reconstructing an attenuation corrected PET image. The systems and methods may reconstruct the attenuation corrected PET image based on PET data and an anatomical image. The anatomical image may include a CT image or an MR image. For illustration purposes, the reconstruction of an attenuation corrected PET image based on the CT image is described as an example in the present disclosure. The PET data and the CT image may correspond to a same scanning region of the subject. The PET data may be gated to reconstruct a plurality of gated PET images corresponding to a plurality of respiratory phases. One or more sub-regions corresponding to at least a portion of a lung and at least a portion of a liver of the subject may be identified in the CT image. Based on the sub-regions, a reference respiratory phase of the CT image may be determined among the plurality of the respiratory phases. A gated PET image corresponding to a target respiratory phase may be registered with a reference gated PET image corresponding to the reference respiratory phase to determine a motion vector field corresponding to the target respiratory phase with respect to the reference respiratory phase. The CT image may be transformed based on the motion vector field to generate a respiratory phase-matched CT image corresponding to the target respiratory phase. An attenuation corrected PET image corresponding to the target respiratory phase may be reconstructed based on the gated PET data and the respiratory phase-matched CT image corresponding to the target respiratory phase.

According to some embodiments of the present disclosure, the CT image may be generated by performing a spiral CT scan. The CT image may include a plurality of sub-CT images each of which corresponds to one of a plurality of portions of the subject. Each of the plurality of gated PET images may include a plurality of sub-gated PET images each of which corresponds to one of the plurality of portions of the subject. A target motion vector field between a target respiratory phase among the plurality of respiratory phases and a respiratory phase of the CT image based on the plurality of sub-gated PET images and the plurality of sub-CT images. An attenuation corrected PET image corresponding to the target respiratory phase may be reconstructed based on the target motion vector field, the CT image, and PET data used for the plurality of gated PET images reconstruction. Since the CT image is acquired by performing the spiral CT scan, different sub-CT images may correspond to different respiratory phases. In such cases, the CT image may correspond to a hybrid respiratory phase, for example, a 3D respiratory phase including the respiratory phase of each of the sub-CT images. By determining the target motion vector field between the target respiratory phase and the respiratory phase of the CT image based on the sub-gated PET images and the sub-CT images, the different respiratory phases of different sub-CT images may be taken into consideration, and the quality of the attenuation corrected PET image corresponding to the target respiratory phase generated may be improved.

FIG. 1 illustrates an exemplary imaging system 100 according to some embodiments of the present disclosure.

An imaging system 100 may acquire an image of a subject. As illustrated, the imaging system 100 may include an imaging device 110, a controller 120, a data processing system 130, an input/output device 140, a network 160, and a terminal(s) 170, a gating system 180, and storage 190.

In some embodiments, the imaging device 110 may scan a subject, and acquire data relating to the subject. In some embodiments, the imaging device 110 may be, for example, a PET device, a CT device, an MRI device, or the like, or any combination thereof (e.g., a PET-CT device, a PET-MRI device, or a CT-MRI device). In some embodiments, the imaging device 110 may be a radiation imaging device. The radiation imaging device may include a radiation source to emit radioactive rays to the subject to be scanned. The radioactive rays may include, for example, particle rays, photon rays, or the like, or any combination thereof. The particle rays may include neutrons, protons, electrons, μ-mesons, heavy ions, or the like, or any combination thereof. The photon rays may include X-ray, γ-ray, α-ray, β-ray, ultraviolet, laser, or the like, or any combination thereof.

In some embodiments, the imaging device 110 may be a PET/CT imaging device including a gantry 111, a detector 112, a field of view (FOV) 113, a table 114, and a radiation source 115. The gantry 111 may support the detector 112 and the radiation source 115. A subject may be placed on the table 114 and moved into the FOV 113 for scanning along the z-axis as illustrated in FIG. 1. The radiation source 115 may emit radioactive rays to the subject. The detector 112 may detect radiation events (e.g., gamma photons) emitted from the FOV 113. In some embodiments, the detector 112 may include one or more detector units. The detector 112 may include a scintillation detector (e.g., a cesium iodide detector), a gas detector, etc. The detector 112 may be and/or include a single-row detector in which a plurality of detector units are arranged in a single row and/or a multi-row detector in which a plurality of detector units are arranged in multiple rows.

The controller 120 may control the imaging device 110, the input/output device 140, and/or the data processing system 130. In some embodiments, the controller 120 may control the X-ray generation unit and/or the X-ray detection unit (if any) of the imaging device 110. The controller 120 may receive information from or send information to the imaging device 110, the input/output device 140, and/or the data processing system 130. For example, the controller 120 may receive commands from the input/output device 140 provided by a user. As a further example, the controller 120 may control the imaging device 110, the input/output device 140, and/or the data processing system 130 according to the received commands or transformed commands. As still a further example, the controller 120 may send image signals or data to the data processing system 130. In some embodiments, the controller 120 may include a computer, a program, an algorithm, software, a storage device, one or more interfaces, etc. Exemplary interfaces may include the interfaces with the imaging device 110, the input/output device 140, the data processing system 130, and/or other modules or units in the imaging system 100.

In some embodiments, the controller 120 may receive a command provided by a user including, for example, an imaging technician, a doctor, etc. Exemplary commands may relate to a scan time, a location of the subject, the location of a table on which the subject lies, a rotation speed of the gantry, a specific parameter relating to a threshold that may be used in the image reconstruction process, or the like, or any combination thereof. In some embodiments, the controller 120 may control the data processing system 130 to select different algorithms to process the raw data of an image.

The data processing system 130 may process information received from the imaging device 110, the controller 120, the input/output device 140, and/or the terminal 170. In some embodiments, the data processing system 130 may reconstruct a CT image and/or a PET image based on the information acquired by the imaging device 110. The data processing system 130 may deliver the images to the input/output device 140 for display. In some embodiments, the data processing system 130 may perform operations including, for example, data preprocessing, image reconstruction, image correction, image composition, lookup table creation, or the like, or any combination thereof. In some embodiments, the data processing system 130 may process data based on an algorithm including, for example, the Fourier slice theorem, a filtered back projection algorithm, fan-beam reconstruction, iterative reconstruction, or the like, or any combination thereof. Merely by way of example, image data regarding a lung may be processed in the data processing system 130. In some embodiments, the data processing system 130 may generate a reconstructed PET image based on a CT image. In some embodiments, artifacts may appear in the PET image because of a mismatch of the PET data and CT data. The data processing system 130 may apply various algorithms or techniques to reduce the artifacts. For example, the projection data relating to the chest of the object may be processed to reduce the artifacts.

In some embodiments, the data processing system 130 may generate a control signal relating to the configuration of the imaging device 110. In some embodiments, the result generated by the data processing system 130 may be provided to other modules or units in the system including, e.g., the storage 190, a terminal 170, via the network 160.

The input/output device 140 may receive or output information. In some embodiments, an image 150 such as a CT image and/or a PET image generated by the data processing system 130 may be displayed on the input/output device 140. In some embodiments, the input/output device 140 may include a keyboard, a touch screen, a mouse, a remote controller, or the like, or any combination thereof. The input and/or output information may take the form of a program, software, an algorithm, data, text, a number, an image, voice, or the like, or any combination thereof. For example, a user may input some initial parameters or conditions to initiate an imaging process. As another example, some information may be imported from an external resource including, for example, a floppy disk, a hard disk, a wired terminal, a wireless terminal, or the like, or any combination thereof. The output information may be transmitted to a display device, a printer, a storage device, a computing device, or the like, or a combination thereof. In some embodiments, the input/output device 140 may include a graphical user interface. The graphical user interface may facilitate a user to input parameters, and/or intervene in a data processing procedure.

The network 160 may include any suitable network that can facilitate the exchange of information and/or data for the imaging system 100. In some embodiments, one or more components of the imaging system 100 (e.g., the imaging device 110, the controller 120, the data processing system 130, the input/output device 140, and/or the terminal 170, etc.) may communicate information and/or data with one or more other components of the imaging system 100 via the network 160. For example, the data processing system 130 may obtain image data from the imaging device 110 via the network 160. As another example, the data processing system 130 may obtain user instructions from the terminal 170 via the network 160.

The network 160 may be and/or include a public network (e.g., the Internet), a private network (e.g., a local area network (LAN), a wide area network (WAN), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 160 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 160 may include one or more network access points. For example, the network 160 may include wired and/or wireless network access points such as base stations and/or internet exchange points through which one or more components of the imaging system 100 may be connected to the network 160 to exchange data and/or information.

The terminal(s) 170 may include a mobile device 171, a tablet computer 172, a laptop computer 173, or the like, or any combination thereof. In some embodiments, the mobile device 171 may include a smart home device, a wearable device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device 171 may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 170 may be part of or communicate with the data processing system 130.

The gating system 180 may collect information relating to, for example, breathing, heartbeat, etc. The gating system 180 may analyze the information to obtain a motion signal including, for example, a respiration signal, a cardiac motion signal, etc. The gating system 180 may include a gating camera for detecting a motion of the subject, a control panel, a marker on a surface of the subject for indicating a motion of the subject, or the like, or any combination thereof. In some embodiments, the gating camera may be an infrared camera. For example, when the imaging device 110 is scanning a patient, the gating system may be triggered automatically. The gating system 180 may collect information associated with the respiration motion of the subject during the scanning. The data collected by the gating system 180 may be stored together with the PET data or CT data.

In some embodiments, the imaging device 110, the controller 120, the data processing system 130, the input/output device 140, the terminal 170, and the gating system 180 may be connected to or communicate with each other directly. In some embodiments, the imaging device 110, the controller 120, the data processing system 130, the input/output device 140 may be connected to or communicate with each other via a network 160. In some embodiments, the imaging device 110, the controller 120, the data processing system 130, the input/output device 140 may be connected to or communicate with each other via an intermediate unit (not shown in FIG. 1). The intermediate unit may be a visible component or an invisible field (radio, optical, sonic, electromagnetic induction, etc.). The connection between different units may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), or the like, or any combination thereof. The network 160 may be used in connection with the present system described herein are not exhaustive and are not limiting.

The storage 190 may store information related to the imaging system 100. In some embodiments, the storage 190 may perform some storage-related functions, such as data consolidation and/or data pre-processing. The storage 190 may acquire information from or output information to other modules. The information stored in storage 190 may be acquired from or output to an external resource, such as a floppy disk, a hard disk, a CD-ROM, a network server, a cloud server, a wireless terminal, or the like, or any combination thereof.

The storage 190 may store information by way of electric, magnetic, optical energy, or virtual storage resources, etc. The storage module that stores information by way of electric energy may include Random Access Memory (RAM), Read Only Memory (ROM), flash memory, or the like, or any combination thereof. The storage module that stores information by way of magnetic energy may include a hard disk, a floppy disk, a magnetic tape, a magnetic core memory, a bubble memory, a USB flash drive, or the like, or any combination thereof. The storage module that stores information by way of optical energy may include CD (Compact Disk), VCD (Video Compact Disk), or the like, or any combination thereof. The storage module that stores information by way of virtual storage resources may include cloud storage, a virtual private network, and/or other virtual storage resources. The method to store information may include sequential storage, link storage, hash storage, index storage, or the like, or any combination thereof.

It should be noted that the above description of the imaging system 100 is merely an example, and should not be understood as the only embodiment. To those skilled in the art, after understanding the basic principles of the connection between different units, the units, and connection between the units may be modified or varied without departing from the principles. The modifications and variations are still within the scope of the current application described above. In some embodiments, these units may be independent, and in some embodiments, part of the units may be integrated into one unit to work together. In some embodiments, the imaging device 110 may be used in internal inspection of components including e.g., flaw detection, security scanning, failure analysis, metrology, assembly analysis, void analysis, wall thickness analysis, or the like, or any combination thereof.

Figure 2:
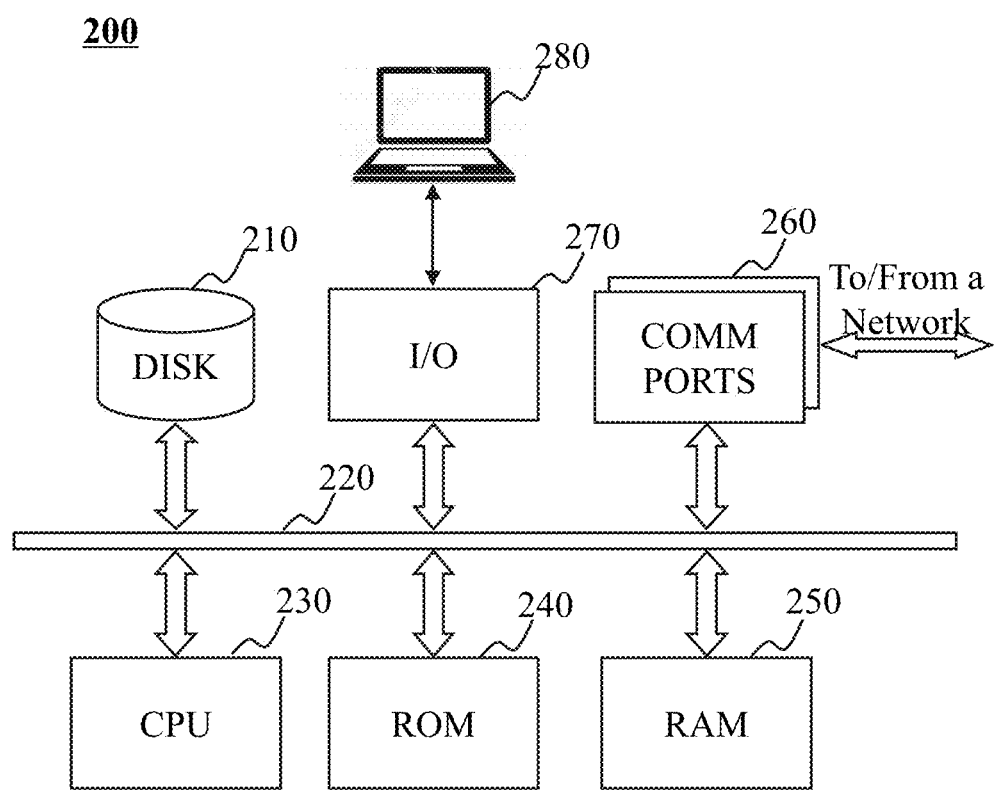
FIG. 2 is a schematic diagram illustrating exemplary hardware and software components of a computing device on which data processing system or a portion thereof may be implemented according to some embodiments of the present disclosure.

FIG. 2 is a schematic diagram illustrating exemplary hardware and software components of a computing device 200 on which data processing system 130 or a portion thereof may be implemented according to some embodiments of the present disclosure. For example, the processing system 130 or the processing module 440 of the processing system 130 may be implemented on the computing device 200 and configured to perform functions of the data processing system 130 described in this disclosure.

The computing device 200 may be a general-purpose computer or a special purpose computer, both may be used to implement an imaging processing system for the present disclosure. The computing device 200 may be used to implement any component for image processing as described herein. For example, the data processing system 130 may be implemented on the computing device 200, via its hardware, software program, firmware, or any combination thereof. Although only one such computer is shown, for convenience, the computer functions relating to the image processing as described herein may be implemented in a distributed fashion on a number of similar platforms, to distribute the processing load.

The computing device 200, for example, may include communication (COMM) ports 260 connected to and from a network to facilitate data communications. The computing device 200 may also include a processor 230 (e.g., a central processing unit (CPU)), in the form of one or more processors, for executing program instructions. The exemplary computer platform may include an internal communication bus 220, program storage and data storage of different forms, for example, a disk 210, and a read only memory (ROM) 240, or a random-access memory (RAM) 250, for various data files to be processed and/or transmitted by the computer. The exemplary computer platform may also include program instructions stored in the ROM 240, RAM 250, and/or another type of non-transitory storage medium to be executed by the processor 230. The methods and/or processes of the present disclosure may be implemented as the program instructions. The computing device 200 also includes an I/O component 270, supporting input/output between the computer and other components therein such as user interface elements 280. The computing device 200 may also receive programming and data via network communications.

Merely for illustration, only one processor is illustrated in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two different processors jointly or separately in the computing device 200 (e.g., the first processor executes operation A and the second processor executes operation B, or the first and second processors jointly execute operations A and B).

Figure 3:
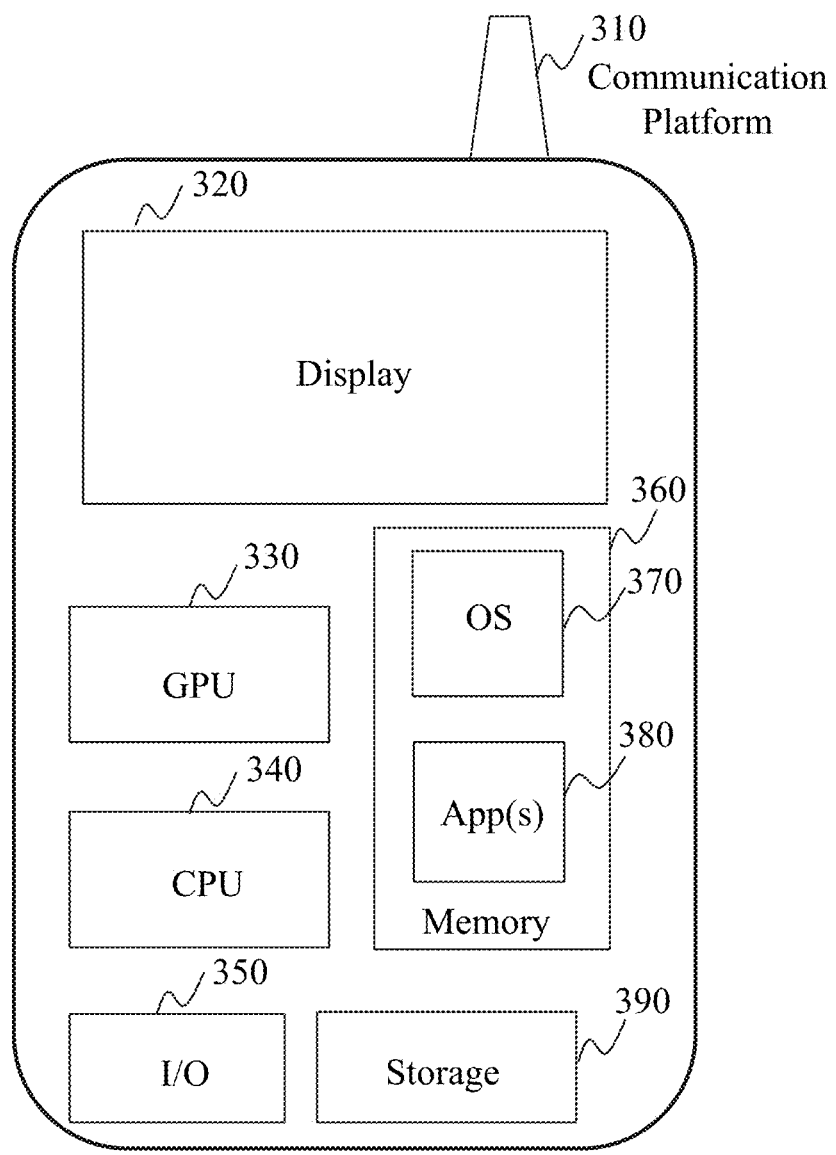
FIG. 3 is a schematic diagram illustrating exemplary hardware and/or software components of a mobile device on which a user terminal may be implemented according to some embodiments of the present disclosure.

FIG. 3 is a schematic diagram illustrating exemplary hardware and/or software components of an exemplary mobile device 300 on which a terminal 170 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, an operation system (OS) 370, applications 380, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the data processing system 130. User interactions with the information stream may be achieved via the I/O 350 and provided to the data processing system 130 and/or other components of the imaging system 100 via the network 160.

Figure 4:
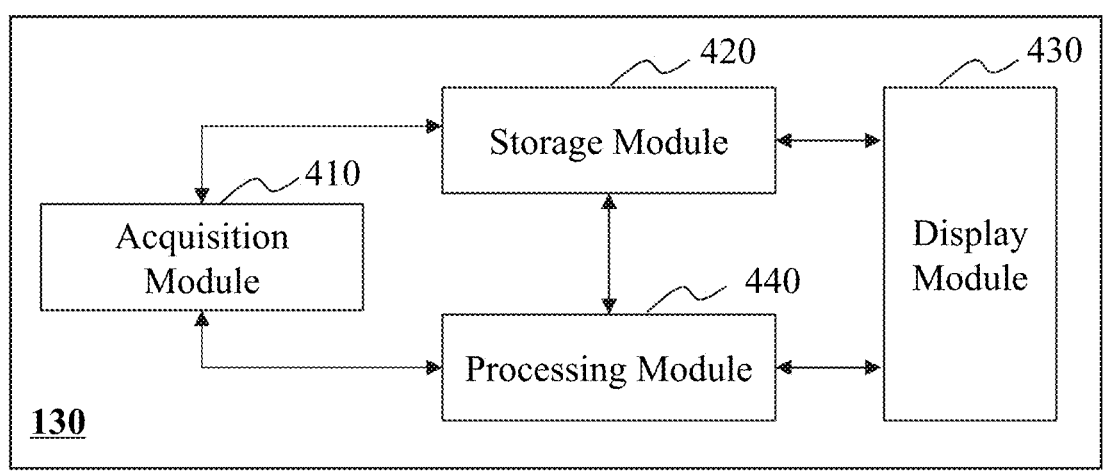
FIG. 4 is a block diagram illustrating an exemplary data processing system according to some embodiments of the present disclosure.

FIG. 4 is a block diagram illustrating an exemplary data processing system 130 according to some embodiments of the present disclosure. As shown in FIG. 4, the data processing system 130 may include a acquisition module 410, a storage module 420, a display module 430, and a processing module 440. At least a portion of the data processing system 130 may be implemented on the computing device 200 as illustrated in FIG. 2, or the mobile device 300 as illustrated in FIG. 3.

The acquisition module 410 may acquire data. The data may be acquired from one or more components of the imaging system 100, such as the imaging device 110 and/or the controller 120. In some embodiments, the data may be acquired from an external data source via the network 160. The data acquired may be 4D image data, 3D image data, and/or 2D image data. The data acquired may include information regarding a whole human body, a lung, a bronchus, a thorax, or the like, or any combination thereof. In some embodiments, the acquisition module 410 may include a wireless receiver to receive data via the network 160.

The storage module 420 may store data. The data stored may be a numerical value, a signal, an image, information of a subject, an instruction, an algorithm, or the like, or a combination thereof. The data stored may be acquired by the acquisition module 410, imported via the input/output device 140, generated in the processing module 440, or pre-stored in the storage module 420 during system initialization or before an operation of data processing. The storage module 420 may include a system storage device (e.g., a disk) that is provided integrally (i.e. substantially non-removable), or a storage device that is removable connectable to the system via, for example, a port (e.g., a UBS port, a firewire port, etc.), a drive (a disk drive, etc.), etc. The storage module 420 may include, for example, a hard disk, a floppy disk, selectron storage, random access memory (RAM), dynamic random access memory (DRAM), static random access memory (SRAM), bubble memory, thin film memory, magnetic plated wire memory, phase change memory, flash memory, a cloud disk, or the like, or a combination thereof. The storage module 420 may be connected to or communicate with one or more of the acquisition module 410, the processing module 440, and the display module 430. In some embodiments, the storage module 420 may be operationally connected with one or more virtual storage resources (e.g., cloud storage, a virtual private network, other virtual storage resources, etc.) via the network 160.

The display module 430 may display information. The information displayed may include a value, a text, an image, and information of a subject. The information displayed may be transmitted from the acquisition module 410, the storage module 420, and/or the processing module 440. In some embodiments, the display module 430 may transform information to the input/output device 140 for display. In some embodiments, the display module 430 may transform the image data that is generated from the processing module 440 for display. In some embodiments, the display module 430 may transform the image data directly retrieved from the storage module 420 or from an external data source via the network 160 for display.

The processing module 440 may process data and generate an image. The data may be acquired from the acquisition module 410, the storage module 420, etc. The image may be transmitted by the processing module 440 to the display module 430. In some embodiments, the data processed may be acquired from an external data source via the network 160. In some embodiments, the processing module 440 may reconstruct image data to generate one or more images. In some embodiments, the processing module 440 may segment an image.

In some embodiments, the processing module 440 may include a universal processor, e.g., a programmable logic device (PLD), an application-specific integrated circuit (ASIC), a microprocessor, a system on chip (SoC), a digital signal processor (DSP), or the like, or any combination thereof. Two or more of these universal processors in the processing module 440 may be integrated into a hardware device, or two or more hardware devices independently with each other. It should be understood, the universal processor in the processing module 440 may be implemented via various configurations. For example, in some embodiments, the processing procedure of the processing module 440 may be implemented by hardware, software, or a combination of hardware software, not only by a hardware circuit in a programmable hardware device in an ultra large scale integrated circuit, a gate array chip, a semiconductor such a transistor, or a field programmable gate array, a programmable logic device, and also by a software performed by various processors, and also by a combination of the hardware and the software above (e.g., firmware).

It should be noted that the above description of the data processing system 130 is merely an example, and should not be understood as the only embodiment. To those skilled in the art, after understanding the basic principles of the connection between different units, the units and connection between the units may be modified or varied without departing from the principles. The modifications and variations are still within the scope of the current application described above. For example, the display module 430 may be omitted.

Figure 5:
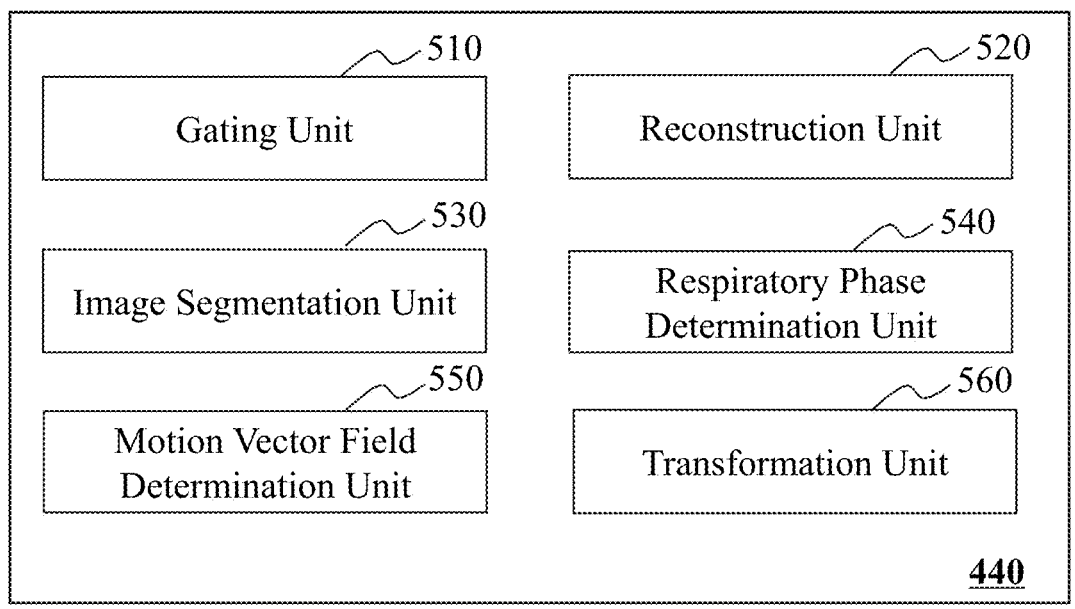
FIG. 5 is a block diagram illustrating an exemplary processing module according to some embodiments of the present disclosure.

FIG. 5 is a block diagram illustrating an exemplary processing module 440 according to some embodiments of the present disclosure. The processing module 440 may include a gating unit 510, a reconstruction unit 520, an image segmentation unit 530, a respiratory phase determination unit 540, a motion vector field determination unit 550, and a transformation unit 560.

In some embodiments, the processing module 440 may be implemented on the processor 230 in the computing device 200, the CPU 340 in the mobile device 300, or any component of the imaging system 100. At least a portion of the processing module 440 may be implemented on the computing device 200 as illustrated in FIG. 2 or the mobile device 300 as illustrated in FIG. 3. A module may be a hardware circuit that is designed to perform one or more of the following actions, a set of instructions stored in one or more storage media, and/or any combination of the hardware circuit and the one or more storage media.

The gating unit 510 may gate (or bin) PET data into a plurality of groups or phase frames of gated PET data. The PET data may be the projection data of a PET scanning. For example, the PET data may be generated by scanning the thorax of a patient using the imaging system 100 (e.g., a PET imaging system). The PET data may be obtained from the acquisition module 410, or any other components of the imaging system 100. In some embodiments, the PET data may be transmitted or received in the form of an electronic signal. The electronic signal may be used to encode the PET data. Merely by way of example, the PET data may be retrieved from a cloud storage (e.g., a public cloud) via the network 160.

In some embodiments, the PET data may correspond to CT data or a CT image. For instance, the PET data and the CT data and/or CT image may be obtained by scanning a same region of a same subject (for example, a patient). The CT data may be obtained by scanning a patient before or after a PET scanning of the patient at (essentially) the same patient position. As used herein, a patient position may refer to a position of a subject on a table (e.g., the table 114) during a scan (e.g., a CT scan and/or a PET scan).

In some embodiments, the PET data may be gated or binned based on a gating condition. In some embodiments, the gating condition may be associated with a type of motion of the subject (or referred to as a subject motion). The subject motion may include a respiratory motion (or referred to as a respiration motion) with a plurality of respiratory phases (related description may be found elsewhere in the present disclosure), a cardiac motion with a plurality of cardiac phases, a gastrointestinal motion with a plurality of gastrointestinal phases, a skeletal muscle motion with a plurality of skeletal muscle motion phases, or the like, or any combination thereof. For example, the subject (e.g., a patient) may undergo respiratory motion during a PET scanning and/or a CT scanning. The methods and systems are described with reference to a respiratory motion for illustrated purposes, and not intended to limit the scope of the present disclosure. The systems and methods disclosed herein may be applied in the context of other motion types including, for example, cardiac motion, gastrointestinal motion, skeletal muscle motion, etc., or a combination thereof.

The gating condition may include a gating parameter, a time interval, a region of interest, a compression algorithm, or the like, or any combination thereof. The gating parameter may include a respiratory phase, a cardiac phase, a gastrointestinal phase, a skeletal muscle motion phase, or the like, or any combination thereof. The respiratory phase may correspond to the respiratory motion of the subject (e.g., the patient). The respiratory motion of the subject may include an inhaling phase (or referred to as an inspiratory phase) and/or an exhaling phase (or referred to as an expiratory phase). For example, in the inhaling phase, the patient may expand his/her chest to cause a negative pressure in the chest. The negative pressure may cause the air to flow into the lungs of the patient. As another example, in the exhaling phase, the patient may shrink the chest to cause a positive pressure in the chest. The positive pressure may push the air out of the lungs.

In some embodiments, the gating unit 510 may gate the PET data by dividing the PET data into a plurality of groups or frames based on a time interval associated with a respiratory motion. The time interval may be determined based on the amplitudes of the respiratory motion, the variation of the amplitudes with time, etc. For example, in a respiratory cycle, from an end-expiration to an end-inspiration, the motion amplitude may increase from a lowest value to a highest value. An average value of the lowest value and the highest value may be determined to be a midway amplitude. In this case, a first time interval may be determined to be the time period between the time point corresponding to an end-expiration and the time point corresponding to the midway amplitude that first appears during the respiration motion after the end-expiration. A second time interval may be determined to be the time period between the time point corresponding to the timing of the midway amplitude and the time point corresponding to the end-inspiration that first appears during the respiration motion after the midway amplitude. Similarly, the number of groups may vary, a group of PET data corresponding to a time interval that in turn corresponds to a range of respiratory motion amplitudes of the subject. In some embodiments, the time interval may be a constant.

In some embodiments, the gating unit 510 may divide the PET data based on the motion information acquired by the gating system 180. The gating system 180 may include a device for detecting a motion of the subject, a control panel, a marker on a surface of the subject for indicating a motion of the subject, or the like, or any combination thereof. In some embodiments, the gating system 180 may include a motion detection device, such as a gating camera (e.g., an infrared camera), a belt secured around the chest of the subject, or another pressure measurement technique or device to measure the change of pressure during the breathing cycles of the subject. The gating system 180 may be used to collect information relating to, for example, respiration, heartbeat, etc. The gating system 180 may analyze the information to obtain the gating parameter (e.g., the respiratory phase). In some embodiments, motion information may be derived from the imaging data including, for example, PET data. Exemplary gating techniques, including self-gating, may be found in, for example, U.S. application Ser. No. 15/386,048 filed Dec. 21, 2016, and Ser. No. 15/616,425 filed Jun. 9, 2017, both entitled "METHODS AND SYSTEMS FOR EMISSION COMPUTED TOMOGRAPHY IMAGE RECONSTRUCTION," the contents of each of which are hereby incorporated by reference.

The reconstruction unit 520 may reconstruct one or more gated PET images based on the gated PET data corresponding to different respiratory phases. Additionally or alternatively, the reconstruction unit 520 may reconstruct an attenuation corrected PET image corresponding to a respiratory phase based on the gated PET data and a CT image (or a respiratory phase-matched CT image as described elsewhere in the present disclosure) corresponding to the respiratory phase. In some embodiments, the attenuated corrected gated PET image may integrate information of the gated PET data and the CT image (or the respiratory phase-matched CT image). The anatomical information of the subject may be obtained from the CT image (or the respiratory phase-matched CT image), and the functional information may be obtained from the gated PET data. The reconstruction unit 520 may generate an attenuation map including a plurality of attenuation coefficients based on the CT image (or the respiratory phase-matched CT image). The attenuation map may be used to correct the gated PET data. The reconstruction unit 520 may then reconstruct an attenuated corrected PET image corresponding to the respiratory phase based on the gated PET data and the corresponding attenuation map.

In some embodiments, the reconstruction unit 520 may use a reconstruction algorithm to reconstruct a gated PET image and/or a PET image. Exemplary reconstruction algorithms may include a maximum-likelihood reconstruction of attenuation and activity (MLAA) algorithm, an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof.

The image segmentation unit 530 may segment an image. For example, the image segmentation unit 530 may identify one or more VOIs or sub-regions in a CT image by segmenting the CT image. In some embodiments, the image segmentation unit 530 may segment an image based on an image segmentation technique. Exemplary image segmentation techniques may include an edge detection technique, a threshold segmentation technique, a histogram-based segmentation technique, a clustering segmentation technique, a compression-based segmentation technique, a region-growing segmentation technique, a graph partitioning technique, or the like, or a combination thereof. In some embodiments, the edge detection technique may be performed based on an edge detection algorithm, for example, a Sobel edge detection algorithm, a Canny edge detection algorithm, a phase congruency-based algorithm, or the like, or a combination thereof.

The respiratory phase determination unit 540 may determine a respiratory phase of a CT image. In some embodiments, the respiratory phase of the CT image may be determined based on a plurality of gated PET images that corresponds to a same scanning region of a subject as the CT image. The gated PET images may correspond to a plurality of respiratory phases. The respiratory phase determination unit 540 may determine a reference respiration phase of the CT image among the respiratory phases of the gated PET images. The reference respiratory phase may be designated as the respiratory phase of the CT image. The reference respiration phase may be any one of the respiratory phases of the gated PET images. In some embodiments, the reference respiration phase may be determined based on similarities between the CT image (or a portion thereof) and the gated PET images (or a portion thereof). In some embodiments, the similarity may include a pixel-based similarity, an entropy-based similarity, a mutual information similarity, or the like, or any combination thereof.

In some embodiments, when the CT image is acquired by performing a spiral CT scan on the subject, the respiratory phase (or physiological phase) of the CT image may include a reference respiratory phase of each of a plurality of sub-CT images of the CT image. The respiratory phase determination unit 540 may determine the reference respiratory phase of each of the plurality of sub-CT images based on a plurality of sub-gated PET images of the plurality of gated PET images. Each sub-gated PET image may correspond to one of the plurality of sub-CT images.

The motion vector field determination unit 550 may determine a motion vector field between two images by registering the two images. For example, the motion vector field determination unit 550 may register two gated PET images corresponding to different respiratory phases. In some embodiments, the motion vector field determination unit 550 may register one or more gated PET images with a reference gated PET image. The reference gated PET image may be one of the gated PET images corresponding to a reference respiratory phase of a CT image.

The registration may be implemented based on at least one registration algorithm. Exemplary registration algorithms may include a point-based registration algorithm (e.g., an anatomic-landmark-based registration algorithm), a curve-based registration algorithm, a surface-based registration algorithm (e.g., a surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow, demons registration algorithm, B-spline registration algorithm, or the like, or any combination thereof. In some embodiments, the registration may be performed based on a rigid transformation, an affine transformation, a projection transformation, a nonlinear transformation, an optical-flow-based registration, a similarity measurement, or the like, or any combination thereof. The similarity measurement may include a mutual-information-based measurement, a Fourier-analysis-based measurement, or the like, or any combination thereof.

In some embodiments, the motion vector field determination unit 550 may determine a motion vector field between two gated PET images corresponding to different respiratory phases. The motion vector field may include a plurality of motion vectors. A motion vector may be used to describe the motion of a spatial point of the subject between two respiratory phases corresponding to the two gated PET images. In some embodiments, a motion vector may be determined by registering the two gated PET images. For example, after the two gated PET images are registered, locations of two voxels in the gated PET images corresponding to a same spatial point of the subject may be determined. Then the motion vector field determination unit 550 may determine the corresponding motion vector of the spatial point based on the locations of the two voxels. A motion vector field may include a portion or all of the motion vectors between two gated PET images. The motion vector field may be used to describe a motion relationship of spatial points between two respiration phases corresponding to the two gated PET images.

In some embodiments, the motion vector field determination unit 550 may determine a target motion vector field between a target respiratory phase and a respiratory phase of the CT image based on the plurality of sub-gated PET images and the plurality of sub-CT images. For example, the motion vector field determination unit 550 may determine a motion vector field between the target respiratory phase and the reference respiratory phase of each sub-CT image. Based on the motion vector field corresponding to each sub-CT image, the motion vector field determination unit 550 may further determine the target motion vector field between the target respiratory phase and the respiratory phase of the CT image. The target motion vector field may be a hybrid motion vector field including the motion vector field corresponding to each sub-CT image.

The transformation unit 560 may transform an image or a portion thereof based on a motion vector field. For example, the transformation unit 560 may transform a CT image of a first respiratory phase (e.g., a reference respiratory phase) based on a motion vector field between the first respiratory phase and a second respiratory phase. The transformed CT image may be regarded as a respiratory phase-matched CT image corresponding to the second respiratory phase. In some embodiments, the transformation unit 560 may transform a VOI in the CT image of a subject. The VOI to be corrected may correspond to, for example, a portion of the scanning region of the CT image that excludes one or more bones of the subject. In some embodiments, the VOI to be corrected may correspond to at least part of a thoracic and abdominal region of the subject.

It should be noted that the above descriptions of the processing module 440 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, two or more units may be integrated into one unit to perform the functions thereof.

Figure 6:
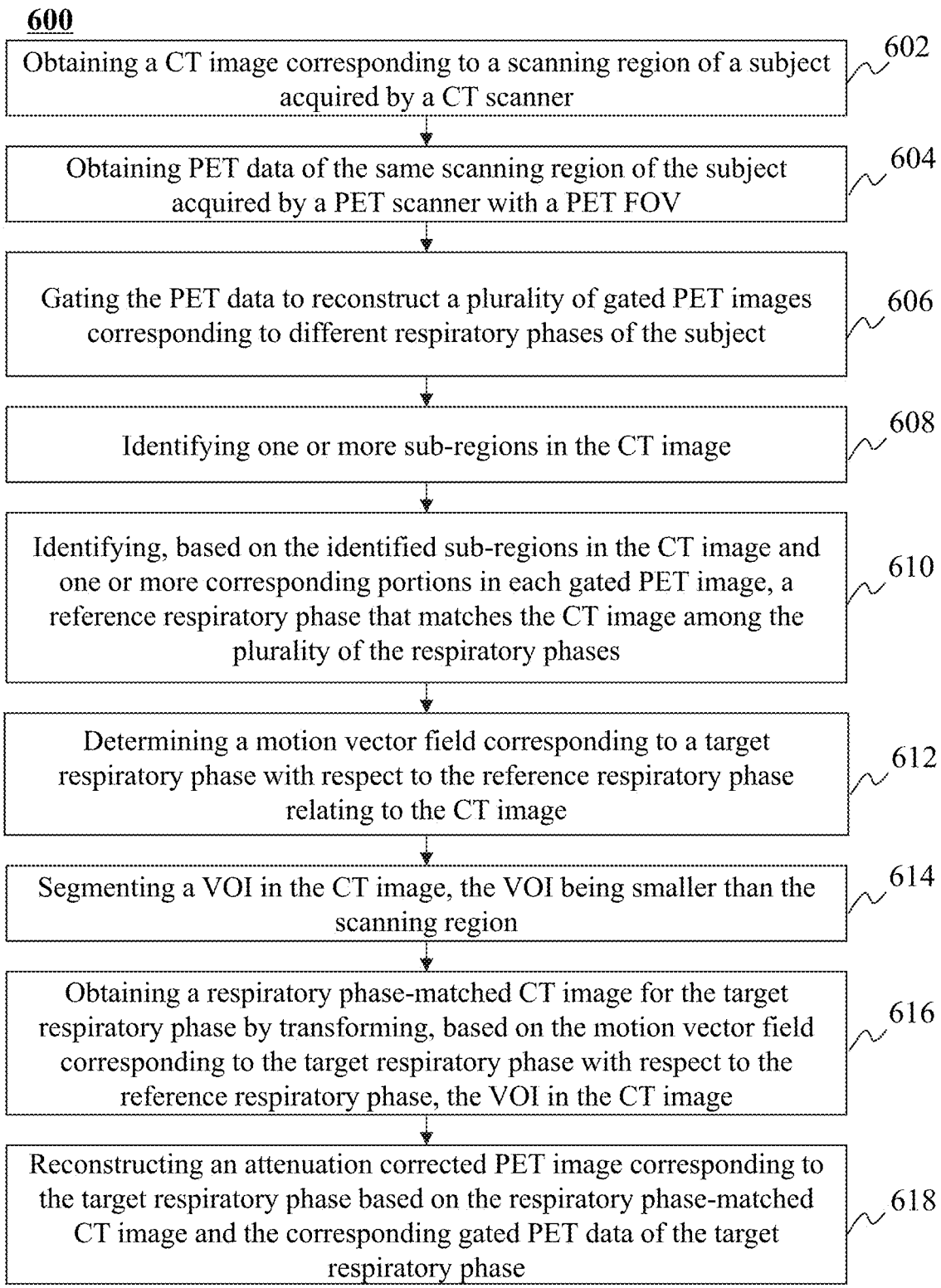
FIG. 6 is a flowchart illustrating an exemplary process for reconstructing an attenuation corrected PET image according to some embodiments of the present disclosure.

FIG. 6 is a flowchart illustrating an exemplary process for reconstructing an attenuation corrected PET image corresponding to a target respiratory phase according to some embodiments of the present disclosure. At least a portion of process 600 may be implemented on the computing device 200 as illustrated in FIG. 2 or the mobile device 300 as illustrated in FIG. 3. In some embodiments, one or more operations of process 600 may be implemented in the imaging system 100 as illustrated in FIG. 1. For example, the process 600 may be stored in the storage module 420 of the data processing system 130 in the form of instructions, and invoked and/or executed by the data processing system 130 (e.g., the processor 230 of the data processing system 130).

In some embodiments, the attenuation corrected PET image of a subject (e.g., a patient) may be reconstructed based on CT data and PET data of the subject. The CT data may be applied in the attenuation correction of the PET data. A CT scan usually takes a short time, and a PET scan usually takes a relatively long time. For example, a CT scan may be performed at a speed of about 1.5 seconds/table position. A PET scan may be performed at a speed of about 5 minutes/table position. The subject may undergo a respiratory motion during the CT scan and/or the PET scan. The CT data may be considered to correspond to a respiratory phase because of the short scanning duration. The PET data may correspond to a plurality of respiratory phases, which may lead to a mismatch between the CT data and the PET data. The CT data and the PET data may need to be matched with respect to their corresponding motion phases to reduce motion artifact due to, e.g., the respiratory motion.

In 602, the acquisition module 410 may obtain a CT image corresponding to a scanning region of a subject. The CT image may correspond to a respiratory phase. The subject may include a patient, an animal, a phantom, or a portion thereof including, for example, an artificial limb, an artificial heart, a tumor, any structure or organ that may be examined using X-ray, or the like, or any combination thereof. The scanning region may include any part of the subject. For example, the scanning region may include a whole body of the subject. Alternatively, the scanning region may be a portion of the subject, such as a brain, a lung, a liver, a kidney, a bone, any organ or region of interest (ROI) of the subject. In some embodiments, the scanning region may correspond to at least a portion of a thorax and an abdomen of the subject.

In some embodiments, the CT image may be a 3D CT image including a plurality of 2D CT image layers (e.g., slice images). In some embodiments, the CT image may be a processed CT image (e.g., an attenuation map relating to the CT image). The CT image may be generated based on CT data acquired by a CT scanner, or retrieved from a storage device via the network 160.

In some embodiments, the CT image may be acquired by a CT scanner with a CT field of view (FOV). The CT FOV may refer to an area scanned by the CT scanner during a CT scan. In some embodiments, the CT image may be acquired when at least a portion of a lung and a portion of a liver of the subject are located in a central region of the CT FOV. A portion of the subject is considered to be located at the central region of the CT FOV if it is near a central point of the CT FOV (e.g., a central point of the CT FOV along an axial direction of the CT scanner). The at least a portion of the lung and a portion of the liver of the subject may correspond to one or more sub-regions in the CT image. In some embodiments, at least a portion of the lung and a portion of the liver of the subject may be located within but unnecessarily at the center of the CT FOV. For a PEC/CT device, the CT FOV may be larger than the PET FOV (see, e.g., relevant description of operation 604). To match CT data (or image) and PET data (or image) acquired by the PET/CT device with respect to the same subject (or a portion thereof), the portion of the CT data corresponding to the PET data may be segmented. As used herein, a portion of the CT data (or image) is considered to correspond to the PET data (or image) if they correspond to one or more same spatial points of the subject. The segmented portion of the CT data (or image) may further be used in attenuation correction of the PET data (or image). In some embodiments, the sub-regions in the CT image may serve as a basis for matching the CT data and PET data. When at least a portion of the lung and a portion of the liver are both located in the central region of the CT FOV, the CT image may be more useful in respiratory phase determination compared to CT images containing no lung and/or liver.

In 604, the acquisition module 410 may obtain PET data corresponding to the same scanning region of the subject. As used herein, a CT image and the PET data (or a PET image) are considered to correspond to a same scanning region if the scanning region corresponding to the CT data (or the CT image obtained based on the CT data) at least partially overlaps with the scanning region corresponding to the PET data (or the PET image obtained based on the PET data). The PET data may correspond to the same scanning region as the CT scanning as described in connection with 602. For example, if a CT scan of a chest of the patient is performed, a PET scan of the chest of the patient may be performed when the patient keeps essentially the same patient position, in order to facilitate the combination of information of the PET data and the CT data.

In some embodiments, the PET data may be acquired by a PET scanner with a PET FOV. The PET FOV may refer to an area scanned by the PET scanner during a PET scan. In some embodiments, the PET image may be acquired when at least a portion of a lung and a portion of a liver of the subject are located in a central region of the PET FOV. As such, the reconstructed PET image containing at least a portion of the lung and a portion of the liver may be more helpful in respiratory phase determination than the PET image (or a gated PET image) containing no liver or lung.

In 606, the gating unit 510 may gate the PET data into a plurality of bins corresponding to different respiratory phases of the subject. The reconstruction unit 520 may reconstruct a plurality of gated PET images corresponding to the respiratory phases based on the gated PET data. For example, the respiratory phases of the subject may include an intermediate inspiratory phase, an end-inspiratory phase, an intermediate expiratory phase, an end-expiratory phase, or the like, or any combination thereof. The gated PET images may include a gated PET image corresponding to the intermediate inspiratory phase, a gated PET image corresponding to the end-inspiratory phase, a gated PET image corresponding to the intermediate expiratory phase, a gated PET image corresponding to the end-expiratory phase, or the like, or any combination thereof.

In some embodiments, the gating unit 510 may gate the PET data according to a respiration signal of the subject during the PET scan. The respiration signal may be determined based on the PET data by the gating unit 510, and/or be acquired from another resource (e.g., the gating system 180). The gating unit 510 may divide the respiratory signal into a plurality of respiratory phases based on the amplitude or the time of the respiratory signal. The gating unit 510 may also determine a plurality of groups (or referred to as frames) of gated PET data corresponding to the respiratory phases. The reconstruction module 530 may reconstruct a plurality of gated PET images based on the gated PET data corresponding to the respiratory phases. More descriptions regarding the gating of the PET data and/or the reconstruction of the gated PET images may be found elsewhere in the present disclosure. See, e.g., FIG. 7 and the relevant descriptions thereof.

In 608, the image segmentation unit 530 may identify one or more sub-regions in the CT image. A sub-region in the CT image may include any portion of the CT image. A sub-region may have any size and/or shape. Different sub-regions may have the same or different sizes and/or shapes. In some embodiments, the image segmentation unit 530 may identify a sub-region in the CT image based on an image segmentation technique. Exemplary image segmentation techniques may include an edge detection technique, a threshold segmentation technique, a histogram-based segmentation technique, a clustering segmentation technique, a compression-based segmentation technique, a region-growing segmentation technique, a graph partitioning technique, or the like, or a combination thereof.

In some embodiments, the one or more sub-regions may correspond to at least a portion of a lung and at least a portion of a liver of the subject, and the sub-regions may be smaller than the scanning region. The lung and the liver of the subject have very different attenuation coefficients. If the respiratory motions of the PET data and the CT image are mismatched, the lung and the liver in the CT may have an obvious or visible shift or mismatch with respect to same portions in a PET image (or gated PET image). The sub-regions corresponding to at least a portion of the lung and a portion of the liver may serve as a basis for matching the PET data and the CT image with respect to their respiratory phases.

In some embodiments, the one or more sub-regions may include a first sub-region corresponding to a left lung of the subject and a second sub-region corresponding to a right lung of the subject. For brevity, the first sub-region corresponding to the left lung may be referred to as a left sub-region and the second sub-region corresponding to the right lung may be referred to as a right sub-region.

In some embodiments, the image segmentation unit 530 may segment the left lung and the right lung of the subject from the CT image. The image segmentation unit 530 may then determine the left sub-region based on the left lung and the right sub-region based on the right lung. The segmentation of the left lung and/or the right lung may be performed based on a segmentation technique as described elsewhere in this disclosure. For example, the segmentation of the left lung and/or the right lung may be performed based on a region-growing segmentation technique and/or a threshold segmentation technique.

For illustration purposes, the determination of the left sub-region is described as an example. After identifying the left lung, the image segmentation unit 530 may identify a bottom of the left lung. The bottom of the left lung may border the liver of the subject. Accordingly, the bottom of the left lung may constitute an interface between the left lung and the liver of the subject. The image segmentation unit 530 may further segment a portion of the liver and/or a portion of the stomach beneath the bottom of the left lung. The segmented portion of the liver and/or the stomach beneath the bottom of the left lung may have a predetermined thickness. The image segmentation unit 530 may designate the left lung and the segmented portion of a certain thickness beneath the bottom of the left lung as the left sub-region.

In 610, the respiratory phase determination unit 540 may determine a reference respiratory phase that matches the respiratory phase of the CT image among the plurality of the respiratory phases of the subject. The reference respiratory phase may be determined based on the identified one or more sub-regions in the CT image and corresponding portions in one or more gated PET images of the plurality of gated PET images. In some embodiments, the respiratory phase determination unit 540 may determine a candidate reference respiratory phase for each sub-region, and determine the reference respiratory phase that matches the respiratory phase of the CT image based on the candidate reference respiratory phases. More descriptions regarding the determination of the reference respiratory phase may be found elsewhere in the present disclosure. See, e.g., FIGS. 8A and/or 8B and the relevant descriptions thereof.

In 612, the motion vector field determination unit 550 may determine a motion vector field corresponding to a target respiratory phase with respect to the reference respiratory phase relating to the CT image. The reference respiratory phase relating to the CT image may refer to the reference respiratory phase that matches the respiratory phase of the CT image as described in connection with 610. The motion vector field corresponding to the target respiratory phase with respect to the reference respiratory phase may refer to a motion vector field between a gated PET image corresponding to a target respiratory phase and a reference gated PET image. The reference gated PET image may refer to the gated PET image corresponding to the reference respiratory phase. The reference gated PET image may be reconstructed in 606 or retrieved from a storage device in the imaging system 100 (e.g., the storage 190, the storage module 420) or an external storage device via the internet 160. The target respiratory phase may be any respiratory phase other than the reference respiratory phase.

In some embodiments, the motion vector field determination unit 550 may determine the motion vector field by registering the two gated PET images. For example, the motion vector field determination unit 550 may register the two gated PET images based on a registration algorithm. Exemplary registration algorithms may include a point-based registration algorithm (e.g., an anatomic-landmark-based registration algorithm), a curve-based registration algorithm, a surface-based registration algorithm (e.g., a surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow, or the like, or any combination thereof. In some embodiments, the registration between the two gated PET images may include an automatic registration, a semi-automatic registration, or a manual registration. As used herein, an automatic registration refers to a registration performed automatically by a computing device (e.g., the computing device 200 as illustrated in FIG. 2) without user intervention. As used herein, a semi-automatic registration refers to a registration performed by a computing device (e.g., the computing device 200 as illustrated in FIG. 2) with user intervention. User intervention may include providing information regarding a specific registration algorithm to be used in a registration, a parameter to be used in a registration, or the like, or a combination thereof. For instance, during a semi-automatic registration, a user provides information identifying a characteristic feature (e.g., by marking it on each of the images to be registered on a user interface displaying the images), and a computing device performs the registration based on the information in combination with a registration algorithm and/or parameter. As used herein, a manual registration refers to a registration performed according to instructions provided by a user. For example, via a user interface implemented on, e.g., an input/output device 140 or a mobile device as illustrated in FIG. 3, a user may align the two gated PET images manually to register the two gated PET images. In some embodiments, the registration may be performed based on rigid transformation, an affine transformation, a projection transformation, a nonlinear transformation, an optical-flow-based registration, a similarity measurement, or the like, or any combination thereof.

The motion vector field may include a plurality of motion vectors. A motion vector may be used to describe the motion of a spatial point of the subject between the gated PET image and the reference respiratory phase. For example, the motion vector field determination unit 550 may determine a first location of a spatial point in the gated PET image to be (X1, Y1, Z1), and a second location of the point in the reference gated PET image to be (X2, Y2, Z2). The motion vector field determination unit 550 may further determine a motion vector to be (Ux, Uy, Uz) based on the first location and the second location of the spatial point, where Ux may be equal to (X1-X2), Uy may be equal to (Y1-Y2), and Uz may be equal to (Z1-Z2).

In 614, the image segmentation unit 530 may identify a VOI in the CT image. The VOI may be smaller than the scanning region, and include any portion of the CT image that needs to be corrected to match the gated PET image corresponding to the target respiratory phase.

In some embodiments, the PET data may include a first portion and a second portion. The first portion may be affected more by the respiratory motion of the subject than the second portion. For example, the first portion may correspond to a portion of the scanning region that excludes one or more bones of the subject originally included in the PET data. Merely by way of example, the first portion may correspond to a portion in a thoracic and abdominal region of the subject surrounded by the ribs and the spine of the subject, and the ribs and the spine of the subject may be excluded from the first portion. The second portion may correspond to the portion outside the thoracic and abdominal cavity. As used herein, the thoracic and abdominal region may refer to the region including the thoracic and abdominal cavity and the muscle skin of the ribs and the spine surrounding the thoracic and abdominal cavity. When the subject breaths during a scan, the internal organs within the thoracic and abdominal region may move (the movement may be referred to as a respiratory motion). The portion outside the thoracic and abdominal cavity may undergo no or little respiratory motion. Thus, the first portion may be regarded as being affected more by the respiratory motion than the second portion. The identified VOI in the CT image may correspond to the first portion of the PET data. To match the PET data and the CT image, the VOI may need to be subject to motion transformation and the portion outside the VOI may be omitted from the motion transformation. More descriptions regarding the determination of the VOI may be found elsewhere in the present disclosure. See, e.g., FIG. 9 and the relevant descriptions thereof.

In 616, the transformation unit 560 may obtain a respiratory phase-matched CT image by transforming the VOI in the CT image based on the motion vector field between the gated PET image and the reference gated PET image. The transformed CT image may have a matched respiratory phase (e.g., the same respiratory phase or substantially the same respiratory phase) with the gated PET image. Thus, the transformed CT image may also be referred to as the respiratory phase-matched CT image corresponding to the gated PET image. The motion transformation of the VOI may refer to a transformation of the locations of the voxels in the VOI to reduce the effect of respiratory motions. In the respiratory phase-matched CT image, the VOI may be transformed and voxels outside the VOI may be omitted from the motion transformation and remain their original locations in the CT image. The motion transformation of the VOI may be performed based on the motion vector field between the reference gated PET image and the gated PET image corresponding to the target respiratory phase.

For illustration purposes, the motion vector field between the reference gated PET image and the gated PET image corresponding to the target respiratory phase may be expressed as $(m_u(x,y,z), m_v(x,y,z), m_w(x,y,z))$, where $m_u$ represents the motion vector component in the x-axis direction, $m_v$ represents the motion vector component in the y-axis direction, $m_w$ represents the motion vector component in the z-axis direction. The z-axis may refer to a direction along which an object is moved into and out of a detection tunnel of an imaging device (e.g., a PET/CT scanner). The x-axis and y-axis may form an x-y plane that is perpendicular to the z-axis as illustrated in FIG. 1. The transformation unit 560 may transform the VOI in the CT image to generate a respiratory phase-matched CT image corresponding to the gated PET image by applying the motion vector field to the VOI in the CT image. The transformation of the VOI in the CT image may be performed according to Equation (1) below:

$$C_2(x,y,z)=C(c+m_u(x,y,z),y+m_v(x,y,z),z+m_w(x,y,z)), \quad (1)$$

where $C(x,y,z)$ represents a VOI in the CT image, and $C_2(x,y,z)$ represents the VOI in the respiratory phase-matched CT image corresponding to the gated PET image.

In 618, the reconstruction unit 520 may reconstruct an attenuation corrected PET image corresponding to the target respiratory phase based on the respiratory phase-matched CT image and the gated PET data corresponding to the target respiratory phase. In some embodiments, the reconstruction unit 520 may determine tissue attenuation coefficients corresponding to different portions (e.g., different organs, different tissues) of the subject based on the respiratory phase-matched CT image. The reconstruction unit 520 may generate an attenuation map corresponding to the 511 KeV photon rays (e.g., γ rays) based on the tissue attenuation coefficients. The reconstruction unit 520 may then perform an attenuation correction on the gated PET image based on the attenuation map. The attenuation correction of the gated PET image based on the respiratory phase-matched CT image may also be referred to as a phase-matched attenuation correction of the gated PET image (or gated PET data).

In some embodiments, the reconstruction unit 520 may reconstruct the attenuation corrected PET image corresponding to the target respiratory phase based on a reconstruction algorithm. Exemplary reconstruction algorithms may include an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof.

It should be noted that the above descriptions of the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, one or more operations in the process 600 may be omitted, and/or one or more additional operations may be added. For example, 608 may be omitted. In 610, the respiratory phase determination unit 540 may determine the reference respiratory phase that matches the respiratory phase of the CT image based on the entire CT image and the plurality of gated PET images. As another example, 614 may be omitted. In 616, the transformation unit 560 may transform the entire CT image based on the motion vector field to generate the respiratory phase-matched CT image.

In some embodiments, operations 612 to 618 may be performed for each respiratory phase to generate an attenuation corrected PET images corresponding to each respiratory phase. In some embodiments, the process 600 may include one or more additional operations to reconstruct another attenuation corrected PET image, such as, an attenuation corrected reference PET image, an attenuation corrected average PET image, or the like, or any combination thereof. Exemplary techniques for reconstructing an attenuation corrected PET image may be found in, for example, U.S. application Ser. No. 15/721,783 filed Sep. 30, 2017, entitled "SYSTEMS AND METHODS FOR POSITRON EMISSION TOMOGRAPHY IMAGE RECONSTRUCTION," the contents of which are hereby incorporated by reference. The respiratory phase-matched CT image may be regarded as a corrected CT image in the U.S. application Ser. No. 15/721,783.

In some embodiments, the process 600 may be performed based on an anatomical image other than the CT image. For example, the attenuation corrected gated PET image corresponding to the target respiratory phase may be reconstructed based on PET data and an MR image both corresponding to the same scanning region of the subject. The MR image may be corrected to provide anatomical data of the subject, which may be applied in combination with tissue attenuation coefficients of different portions in an attenuation correction of the PET data. In some embodiments, before operation 608, the MR image may be processed (e.g., filtered, enhanced) so that the organs and/or tissues, such as the bones, lungs, and liver are easier to identify. Operations 608 to 618 may then be performed on the processed MR image to generate the attenuation corrected PET image.

FIG. 7 is a flowchart illustrating an exemplary process for gating PET data according to some embodiments of the present disclosure. In some embodiments, at least a portion of the process 700 may be implemented on the computing device 200 as illustrated in FIG. 2 or the mobile device 300 as illustrated in FIG. 3. In some embodiments, one or more operations of process 700 may be implemented in the imaging system 100 illustrated in FIG. 1. For example, the process 700 may be stored in the storage module 420 of the data processing system 130 in the form of instructions, and invoked and/or executed by the data processing system 130 (e.g., the processor 230 of the data processing system 130). In some embodiments, the process 700 may be performed to achieve operation 606 as described in connection with FIG. 6.

In 710, the gating unit 510 may obtain a respiration signal of the subject during the scanning. The respiration signal may correspond to a plurality of respiratory phases of the subject. In some embodiments, the gating unit 510 may obtain information of a respiratory signal relating to a respiratory motion from the PET data, and determine the respiratory signal of the respiratory motion based on the information.

In some embodiments, the respiration signal may be acquired from a source other than the PET data. For instance, the respiration signal may be obtained from the gating system 180. The gating system 180 may collect information such as breathing information, heartbeat information, etc. The gating system 180 may also analyze the information to determine one or more gating parameters (e.g., the respiratory phase) and/or obtain the respiration signal.

In some embodiments, the respiratory signal may be approximated by a sine function, a cosine function, a polynomial function, a pulse function, or the like, or any combination thereof. In some embodiments, the respiratory signal may be expressed in a two-dimensional coordinate system. The two-dimensional coordinate system may include a first coordinate axis (or the X-axis) representing time, and a second coordinate axis (or the Y-axis) representing amplitude or value. For example, the respiration signal may be approximated by a sine function in the two-dimensional coordinate. The respiration signal may show the amplitude in the Y-axis, and the amplitude may vary depending on the time in the X-axis. In some embodiments, the respiration signal may be approximated by the sine signal or the cosine signal. The gating unit 510 may approximate the respiration signal using, for example, the sine function, the cosine function, etc. For example, the respiration signal may be approximated by Equation (2):

$$Y=c*\sin(aX+b), \quad (2)$$

where Y is the amplitude of the respiratory motion, X is the time of the respiratory motion, and a, b, and c are constant parameters.

In some embodiments, the respiratory signal may be divided into a plurality of respiratory phases. For example, the gating unit 510 may divide the respiratory signal into 4 respiratory phases, each of which may correspond to a different part in a cycle of the respiratory signal. In some embodiments, the gating unit 510 may divide the respiratory signal according to the instruction of a user (e.g., a doctor). The user may provide his/her instruction via a user interface implemented on, e.g., a mobile device as illustrated in FIG. 3.

In some embodiments, the respiratory signal may be divided according to the amplitude of the respiratory signal. For example, a cycle of the respiratory signal may be divided based on the amplitude of the respiratory signal. If the amplitude of the respiratory signal is segmented into n parts (e.g., from the maximum amplitude to the minimum amplitude), the n parts of the respiratory signal may correspond to n respiratory phases. In some embodiments, the respiratory signal may be divided, based on the time of the respiratory signal, into N parts, and the N parts may correspond to N respiratory phases. For example, if a cycle of the respiratory signal lasts 5 seconds, a cycle of the respiratory signal may be divided according to a time interval (e.g., 0.5 seconds, or 1 second), and this cycle of the respiratory signal may be divided into N respiratory phases (e.g., 5/0.5 or 10 respiratory phases, or 5/1 or 5 respiratory phases). Exemplary gating techniques, including self-gating, may be found in, for example, U.S. application Ser. No. 15/386,048 filed Dec. 21, 2016, and Ser. No. 15/616,425 filed Jun. 9, 2017, both entitled "METHODS AND SYSTEMS FOR EMISSION COMPUTED TOMOGRAPHY IMAGE RECONSTRUCTION," the contents of which are hereby incorporated by reference.

In 720, the gating unit 510 may gate the PET data into a plurality of bins based on the plurality of respiratory phases of the respiration signal. The plurality of bins may correspond to the plurality of respiratory phases. For example, the respiratory signal may correspond to N respiratory phases, and the gating unit 510 may gate the PET data into N groups (or frames) of gated PET data based on the N respiratory phases. Each group of gated PET data may correspond to a respiratory phase.

In 730, the reconstruction unit 520 may reconstruct the gated PET data to obtain the plurality of gated PET images corresponding to the plurality of respiratory phases of the subject. In some embodiments, the reconstruction unit 520 may reconstruct a gated PET image for each respiratory phase based on the corresponding group of gated PET data. Alternatively, the reconstruction unit 520 may reconstruct one or more gated PET images for a portion of respiratory phases according to different situations. For example, the reconstruction unit 520 may reconstruct a gated PET image corresponding to an intermediate inspiratory phase.

In some embodiments, the reconstruction unit 520 may use a reconstruction algorithm to reconstruct a gated PET image. Exemplary reconstruction algorithms may include a maximum-likelihood reconstruction of attenuation and activity (MLAA) algorithm, an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof. In some embodiments, the reconstruction unit 520 may generate a gated PET image based on the MLAA algorithm.

In some embodiments, the reconstruction unit 520 may correct a gated PET image based on one or more correction techniques. Exemplary correction techniques may include a random correction technique, a scatter correction technique, a dead time correction technique, or the like, or any combination thereof. In some embodiments, the reconstruction unit 520 may correct a gated PET image based on an attenuation correction technique other than a CT-based attenuation correction technique. For example, the reconstruction unit 520 may perform an attenuation correction of the plurality of gated PET images based on an MLAA algorithm.

FIG. 8A is a flowchart illustrating an exemplary process for determining a reference respiratory phase that matches the respiratory phase of a CT image according to some embodiments of the present disclosure. In some embodiments, process 800A may be performed to achieve operation 610 as described in connection with FIG. 6. In some embodiments, at least a portion of the process 800A may be implemented on the computing device 200 as illustrated in FIG. 2 or the mobile device 300 as illustrated in FIG. 3. In some embodiments, one or more operations of process 800A may be implemented in the imaging system 100 illustrated in FIG. 1. For example, the process 800A may be stored in the storage module 420 of the data processing system 130 in the form of instructions, and invoked and/or executed by the data processing system 130 (e.g., the processor 230 of the data processing system 130).

In 810, for a sub-region, the respiratory phase determination unit 540 may determine a candidate reference respiratory phase of the CT image based on the sub-region and corresponding portions in a plurality of gated PET images. In some embodiments, the respiratory phase determination unit 540 may determine similarities between the sub-region in the CT image and a corresponding portion in each gated PET image. As used herein, a portion of a gated PET image is considered corresponding to a sub-region of the CT image if the portion of the gated PET image corresponds to one or more same spatial points of the subject as the sub-region. The respiratory phase determination unit 540 may determine the candidate reference respiratory phase corresponding to the sub-region based on the determined similarities. More descriptions regarding the determination of a candidate reference respiratory phase corresponding to a sub-region may be found elsewhere in the present disclosure. See, e.g., FIG. 8B and the relevant descriptions thereof. The operation 810 may be repeated for each of the one or more sub-regions of the CT image based on the plurality of gated PET images. For each of the one or more sub-regions of the CT image, a candidate reference respiratory phase may be identified.

In 820, the respiratory phase determination unit 540 may designate one of the candidate reference respiratory phases corresponding to the one or more sub-regions of the CT image as the reference respiratory phase that matches the CT image.

In some embodiments, the candidate reference respiratory phases corresponding to different sub-regions may be the same. The candidate reference respiratory phase may be designated as the reference respiratory phase.

In some embodiments, the candidate reference respiratory phases corresponding to different sub-regions may be different from each other. The candidate reference respiratory phase designated as the reference respiratory phase may be selected from the candidate reference respiratory phases randomly or according to a selection rule. For example, for each of the one or more sub-regions, the respiratory phase determination unit 540 may determine similarities between the sub-region and the corresponding portion in each of the each of the plurality of gated PET images. The respiratory phase determination unit 540 may then determine a variation of the similarities corresponding to each of the one or more sub-regions. The variation of the similarities may be assessed by, for example, a difference between the largest similarity and the smallest similarity among the similarities, a square deviation of the similarities, a standard deviation of the similarities, or the like, or any combination thereof. According to an exemplary selection rule, the respiratory phase determination unit 540 may designate the candidate reference respiratory phase of the sub-region corresponding to the largest variation of the similarities as the reference respiratory phase that matches the respiratory phase of the CT image.

For illustration purposes, the determination of a reference respiratory phase among two candidate reference respiratory phases corresponding to a left sub-region and a right sub-region is described as an example. The left sub-region may include a portion of the left lung and a portion of organs below the left lung of the subject and the right sub-region may include a portion of the right lung and a portion of organs below the right lung of the subject as described in connection with operation 608. The similarities between the left sub-region and the corresponding portion in each of the gated PET images may be determined. The largest similarity and the smallest similarity corresponding to the left sub-region may be denoted as A and B, respectively. The similarities between the right sub-region and the corresponding portion in each of the gated PET images may be determined. The largest similarity and the smallest similarity corresponding to the right sub-region may be denoted as C and D, respectively. If (A−B)>(C−D), the variation of the similarities corresponding to the left sub-region is higher than that of the right sub-region, which may indicate a higher signal-to-noise ratio compared to the determination of a reference respiratory phase based on the left sub-region. Then the candidate reference respiratory phase corresponding to the left sub-region may be designated as the reference respiratory phase. Otherwise, the candidate reference respiratory phase corresponding to the right sub-region may be designated as the reference respiratory phase.

FIG. 8B is a flowchart illustrating an exemplary process for determining a candidate reference respiratory phase for a sub-region according to some embodiments of the present disclosure. In some embodiments, process 800B may be performed to achieve operation 810. In some embodiments, at least a portion of the process 800B may be implemented on the computing device 200 as illustrated in FIG. 2 or the mobile device 300 as illustrated in FIG. 3. In some embodiments, one or more operations of process 800B may be implemented in the imaging system 100 illustrated in FIG. 1. For example, the process 800B may be stored in the storage module 420 of the data processing system 130 in the form of instructions, and invoked and/or executed by the data processing system 130 (e.g., the processor 230 of the data processing system 130).

In 830, for each of the plurality of gated PET images, the respiratory phase determination unit 540 may determine a similarity between a sub-region in the CT image and a corresponding portion in the gated PET image. In some embodiments, the similarity may include a pixel-based similarity, an entropy-based similarity, a mutual information similarity, or the like, or any combination thereof. Merely by way of example, the respiratory phase determination unit 540 may determine the mutual information similarity between the sub-region in the CT image and the corresponding portion of a gated PET image based on Equation (3):

$$MI(C,P_N)=H(C)+H(P_N)-H(C,P_N), \quad (3)$$

where $MI(C,P_N)$ represents the mutual information similarity between the sub-region in the CT image and the corresponding portion in the gated PET image, $H(C)$ represents an entropy of the sub-region in the CT image, $H(P_N)$ represents an entropy of the corresponding portion in the gated PET image, and $H(C,P_N)$ represents a joint entropy of the sub-region in the CT image and the corresponding portion of the gated PET image. When the sub-region in the CT image and the corresponding portion in the gated PET image are irrelevant, the joint entropy may be substantially the same as or similar to a sum of the entropies of the sub-region of the CT image and the corresponding portion in the gated PET image. When the sub-region in the CT image and the corresponding portion in the gated PET image are relevant, the joint entropy may be closer to the larger entropy of the entropy of the sub-region of the CT image and the entropy of the corresponding portion in the gated PET image. In some embodiments, the entropy of the sub-region in the CT image H(C), or the entropy of corresponding portion in the gated PET image $H(P_N)$ may be determined according to Equation (4):

$$H(A)=-\int_0^{+\infty} p_A(v))\log(p_A(v))dv, \quad (4)$$

where $p_A(v)$ represent a histogram of the image A (or a portion thereof). The image A may be the sub-region in the CT image or the corresponding portion in the gated PET image. In some embodiments, $p_A(v)$ of the image A may be determined according to Equation (5):

$$p_A(v)=\iint_{All}\delta(A(x,y)-v)dxdy, \quad (5)$$

where A(x,y) represents a pixel value of a pixel (or a voxel value of a voxel) at (x,y) in the image A, v is a gray value, δ represents a window function centered at 0 (e.g., a Gaussian function with mean 0).

In some embodiments, the joint entropy $H(C,P_N)$ of the sub-region in the CT image and the corresponding portion in the gated PET image of gated N may be determined according to Equation (6):

$$H(C,P_N)=-\iint_0^{+\infty} p_{C,P_N}(v,u)\log(p_{C,P_N}(v,u))dudv, \quad (6)$$

where u represents a pixel value of a pixel (or a voxel value of a voxel) in the sub-region of the CT image, v represents a pixel value of a corresponding pixel (or a voxel value of a corresponding voxel) in the corresponding portion in the gated PET image, and $p_{C,P_N}(v,u)$ is the probability of pixel value (u,v) in the combined histogram of the sub-region in the CT image and the corresponding portion in the gated PET image. A pixel (or voxel) in the gated PET image may be considered corresponding to the pixel (or voxel) in the sub-region of the CT image if they correspond to a same spatial point of the subject. In some embodiments, $p_{C,P_N}(v,u)$ may be determined according to Equation (7):

$$p_{C,P_N}(v,u)=\iint_{CII}\delta(C(x,y)-v)\delta(P_N(x,y)-u)dxdy, \quad (7)$$

where δ represents a window function centered at 0. In some embodiments, the function δ in Equation (5) and Equation (7) may take the form of the Dirac delta function, as determined by Equations (8) and (9):

$$\delta(x) = \begin{cases} +\infty, & x = 0 \\ 0, & x \neq 0 \end{cases}, \quad (8)$$

which is constrained to satisfy the identity:

$$\int_{-\infty}^{+\infty}\delta(x)dx=1. \quad (9)$$

In 840, the respiratory phase determination unit 540 may identify a highest similarity among the determined similarities. In some embodiments, the respiratory phase determination unit 540 may rank the similarities, e.g., from the lowest similarity to the highest similarity, or vice versa, and identify the highest similarity.

In 850, the respiratory phase determination unit 540 may designate the respiratory phase of the gated PET image with the highest similarity as the candidate reference respiratory phase of the CT image. For each of the one or more sub-regions of the CT image, a candidate reference respiratory phase may be determined.

FIG. 9 is a flowchart illustrating an exemplary process for determining a VOI in the CT image according to some embodiments of the present disclosure. In some embodiments, at least a portion of the process 900 may be implemented on the computing device 200 as illustrated in FIG. 2 or the mobile device 300 as illustrated in FIG. 3. In some embodiments, one or more operations of process 900 may be implemented in the imaging system 100 illustrated in FIG. 1. For example, the process 900 may be stored in the storage module 420 of the data processing system 130 in the form of instructions, and invoked and/or executed by the data processing system 130 (e.g., the processor 230 of the data processing system 130). In some embodiments, the process 900 may be performed to achieve operation 614 as described in connection with FIG. 6.

In 910, the image segmentation unit 530 may segment one or more bones surrounding the thoracic and abdominal cavity (or a portion thereof) of the subject. The one or more bones may include one or more ribs and the spine of the subject. In some embodiments, the image segmentation unit 530 may segment the bones based on an image segmentation technique, such as an edge detection technique, a threshold segmentation technique, a histogram-based segmentation technique, a clustering segmentation technique, or the like, or any combination thereof.

In 920, the image segmentation unit 530 may determine one or more edge points of the one or more bones. In some embodiments, the image segmentation unit 530 may determine one or more edge points of the bones on the inside wall of the thoracic and cavity (or a portion thereof). In some embodiments, the image segmentation unit 530 may determine the edge points based on an edge detection algorithm, for example, a Sobel edge detection algorithm, a Canny edge detection algorithm, a phase congruency-based algorithm, or the like, or any combination thereof.

In 930, the image segmentation unit 530 may determine the VOI in the CT image based on the one or more edge points. In some embodiments, the image segmentation unit 530 may generate one or more inner surfaces of the thoracic and cavity based on the edge points of the bones surrounding the thoracic and abdominal cavity of the subject. The image segmentation unit 530 may designate a VOI in the CT image enclosed by the determined surfaces as the VOI. In some embodiments, the surfaces may be determined based on the edge points according to a surface interpolation algorithm, a surface fitting algorithm, or the like, or any combination thereof.

In some embodiments, the image segmentation unit 530 may generate four surfaces around the thoracic and cavity based on the edge points of the bones. The VOI enclosed by the four surfaces may be designated as the VOI in the CT image. The four surfaces may include a right surface, a left surface, a front surface, and a rear surface. The right surface may be a surface determined based on the edge points of the right ribs. The left surface may be a surface determined based on the edge points of the left ribs. The rear surface may be determined based on the edge points of the bones on the back of the subject (i.e., ribs, spine). The subject may have no or few bones in the front portion of the abdomen. The upper part of the front surface may be determined based on the edge points of the bones in the front chest of the subject (i.e., ribs, spines). The lower part of the front surface may be determined based on one or more prophetic edge points that are determined based on a body surface of the subject in the front portion of the abdomen of the subject. In some embodiments, the prophetic edge points may be located at a predetermined distance away from the body surface of the subject in the front portion of the abdomen of the subject.

FIG. 13 is a flowchart illustrating an exemplary process for reconstructing an attenuation corrected PET image corresponding to a target physiological phase according to some embodiments of the present disclosure. In some embodiments, at least a portion of process 1300 may be implemented on the computing device 200 as illustrated in FIG. 2 or the mobile device 300 as illustrated in FIG. 3. In some embodiments, one or more operations of process 1300 may be implemented in the imaging system 100 as illustrated in FIG. 1. For example, the process 1300 may be stored in the storage module 420 of the data processing system 130 in the form of instructions, and invoked and/or executed by the data processing system 130 (e.g., the processor 230 of the data processing system 130).

In 1302, the data processing system 130 (e.g., the acquisition module 410) may obtain a plurality of gated PET images of a subject.

Each of the plurality of gated PET images may correspond to one physiological phase of a plurality of physiological phases of the subject. Each of the plurality of gated PET images may include a plurality of sub-gated PET images each of which corresponds to one of a plurality of portions of the subject. In some embodiments, each gated PET image may be a 3D image. Each gated PET image may be acquired using image reconstruction approach, or time-of-flight histoimaging method.

As used herein, the subject may include a patient, an animal, etc., as described elsewhere in the present disclosure (e.g., FIG. 6 and the descriptions thereof). A physiological phase refers to a phase relating to a physiological movement of the subject. The physiological movement of the subject may include a cardiac motion, a respiratory motion, a blood flow, a gastrointestinal motion, a skeletal muscle motion, a brain motion (e.g., a brain pulsation), or the like, or any combination thereof. For example, the physiological phase may be a cardiac phase relating to the cardiac motion of the subject. A cardiac cycle may include systole (during which the left and right ventricles contract and eject blood into the aorta and pulmonary artery, respectively) and diastole (during which the ventricles are relaxed). The cardiac cycle may be divided into a plurality of cardiac phases, such as 5 or 10 cardiac phases depending on, for example, the heart rate and/or movement amplitude of the heart. As another example, the physiological phase may be a respiratory phase relating to the respiratory motion of the subject. A respiratory cycle may include an inspiratory phase (during which the chest of the subject expands and air flows into the lungs) and an expiratory phase (during which the chest shrinks and the air is pushed out of the lungs). The respiratory cycle may be gated into a plurality of respiratory phases, such as an end-expiration phase, an end-inspiration phase, a deep expiration phase, a deep inspiration phase, one or more middle respiratory phases between the end-expiration phase and the end-inspiration phase, or the like, or any combination thereof. Merely for illustration purposes, the respiratory phase is taken as an example of the physiological phase in the present disclosure. In some embodiments, the terms "physiological phase" and "respiratory phase" can be used interchangeably.

The sub-gated PET images of a gated PET image may correspond to the same physiological phase. For example, for a gated PET image corresponding to an end-inspiration phase, each sub-gated PET image of the gated PET image may correspond to the end-inspiration phase. In some embodiments, the data processing system 130 may divide a gated PET image into a plurality of sub-gated PET images along a specific direction. For example, the gated PET image may be divided into a plurality of sub-gated PET images along a direction perpendicular to an axial plane of the subject. In other words, the subject may be divided into the plurality of portions along the direction perpendicular to the axial plane of the subject. Different portions of the subject may have a same size or different sizes. In some embodiments, the subject may include a plurality of slices, and a portion of the subject may include one or more of the slices. Merely by way of example, the subject may include 100 slices, and each portion may include 10 of the 100 slices.

In some embodiments, the plurality of gated PET images (or a portion thereof) may be reconstructed by the data processing system 130. For example, the data processing system 130 may obtain PET data of the subject acquired by a PET scan of the subject during which the subject is in a breathing status. The data processing system 130 may gate the PET data into a plurality of groups (or referred to as frames) of gated PET data corresponding to the respiratory phases based on a respiration signal of the subject during the PET scan. The data processing system 130 may further reconstruct the plurality of gated PET images based on the groups of gated PET data corresponding to the respiratory phases. More descriptions regarding the reconstruction of the gated PET images may be found elsewhere in the present disclosure. See, e.g., operations 604 and 606 and the relevant descriptions thereof.

In some embodiments, the data processing system 130 may reconstruct a first gated PET image corresponding to the end-inspiration phase based on a group of gated PET data corresponding to the end-inspiration phase, and reconstruct a second gated PET image corresponding to the end-expiration phase based on a group of gated PET data corresponding the end-expiration phase. For each respiratory phase other than the end-inspiration phase and the end-expiration phase, the data processing system 130 may generate a gated PET image corresponding to the respiratory phase based on the first gated PET image and the second gated PET image. For example, a motion vector field (denoted as M1 and also referred to as a first motion vector field) between the end-inspiration phase and the end-expiration phase may be determined based on the first gated PET image and the second gated PET image (e.g., by registering the first gated PET image with the second gated PET image). For a respiratory phase other than the end-inspiration phase and the end-expiration phase, a motion vector field (denoted as M2 and also referred to as a second motion vector field) between the end-inspiration phase (or the end-inspiration phase) and the respiratory phase may be determined based on the motion vector field M1.

In some embodiments, the motion vector field corresponding to a middle respiratory phase may be determined based on the motion vector field M1 according to an interpolation technique. Exemplary interpolation techniques may include a scene-based interpolation technique, an object-based interpolation technique, or the like, or a combination thereof. Exemplary scene-based interpolation techniques may include a linear interpolation technique, a nearest neighbor interpolation technique, a spline interpolation technique, a Kriging interpolation technique, a polynomial interpolation technique, or the like, or any combination thereof. Exemplary object-based interpolation techniques may include a registration-based interpolation technique, a binary voxel-based interpolation technique, a nonrigid registration-based interpolation technique, or the like, or any combination thereof. The motion vector field corresponding to the deep-inspiration phase and/or the motion vector field corresponding to the deep-expiration phase may be determined based on the motion vector field M1 according to an extrapolation technique. Exemplary extrapolation techniques may include a linear extrapolation technique, a polynomial extrapolation technique, a Kriging extrapolation technique, or the like, or any combination thereof. In some embodiments, the gated PET image corresponding to a middle respiratory phase may be reconstructed based on a group of gated PET data corresponding to the middle respiratory phase.

In some embodiments, the plurality of gated PET images (or a portion thereof) may be previously generated by the data processing system 130 or another device and be stored in a storage device (e.g., the storage 190, the storage module 420, or an external storage device). The data processing system 130 may retrieve the gated PET images (or a portion thereof) from the storage device via the network 160.

In 1304, the data processing system 130 (e.g., the acquisition module 410) may obtain a CT image of the subject.

The CT image may be acquired by performing a spiral CT scan on the subject. For example, the CT image may be acquired by a spiral CT device with a CT FOV as described in connection with operation 602 in FIG. 6. The CT image may include a plurality of sub-CT images each of which corresponds to one of the plurality of portions of the subject. As used herein, a sub-CT image and a sub-gated PET image may be regarded as corresponding to each other if they correspond to a same portion of the subject.

In some embodiments, the CT image may be a 3D CT image including a plurality of slice images. Since the CT image is acquired by performing the spiral CT scan, the CT data corresponding to the plurality of slice images of the 3D CT image may be acquired at different time points. In such cases, the plurality of slice images of the 3D CT image may correspond to different physiological phases. In some embodiments, a set of slice images acquired consecutively during the spiral CT scan may include an earliest acquired slice image acquired at a first acquisition time point and a last acquired slice image acquired at a second acquisition time point. If the time difference between the first and second acquisition time points is less than a period, the set of slice images may be considered as corresponding to the same physiological phase.

In some embodiments, a sub-CT image may include one or more slice images, such as a plurality of slice images acquired consecutively during the spiral CT scan. The one or more slice images in the sub-CT image may be considered as corresponding to the same physiological phase (e.g., a same respiratory phase) of the plurality of physiological phases. For example, the CT image may include 1,000 slice images, and one sub-CT image may include 100 slice images corresponding to one physiological phase. As another example, the count of the sub-CT images may be equal to the count of the slice images. In some embodiments, each sub-CT image may include more than a certain count of slice images, which may reduce the amount of computation resources needed for matching the sub-gated PET images and the sub-CT images.

In some embodiments, the plurality of sub-CT images may include different numbers or counts of slice images. For example, a sub-CT image corresponding to a portion near a VOI (e.g., the heart) of the subject may have fewer slice images than a sub-CT image corresponding to a portion far away from the heart. The portion near the VOI may be affected more by a respiratory motion or a cardiac motion of the subject than the portion far away from the heart. As another example, a target portion (e.g., a specific organ or tissue) of the subject may be identified first. A sub-CT image corresponding to a portion that is within a certain distance from the target portion may include fewer slice images than a sub-CT image corresponding to a portion that is out of the certain distance from the target portion.

In some embodiments, the CT image and/or the sub-CT images may be generated by the data processing system 130. For example, the data processing system 130 may obtain CT scan data of the subject acquired during the spiral CT scan, and reconstruct the CT image based on the CT scan data. The data processing system 130 may further divide the CT image into the sub-CT images along a specific direction, such as a direction perpendicular to an axial plane of the subject. For example, the data processing system 130 may divide the CT image into a plurality of sub-CT images according to the acquisition time points of the slice images of the CT image and/or the physical portions that the slice images correspond to. In some embodiments, the data processing system 130 may divide the subject into the plurality of portions, and then divide the CT image into the sub-CT images corresponding to the portions of the subject. In some embodiments, the CT image and/or the sub-CT images may be previously generated by the data processing system 130 or another device and be stored in a storage device (e.g., the storage 190, the storage module 420, or an external storage device). The data processing system 130 may retrieve the CT image and/or the sub-CT images from the storage device via the network 160.

In 1306, the data processing system 130 (e.g., the motion vector field determination unit 550) may determine a target motion vector field between a target physiological phase among the plurality of physiological phases and a physiological phase of the CT image based on the plurality of sub-gated PET images and the plurality of sub-CT images.

As used herein, a physiological phase of the CT image may include a plurality of reference physiological phases of the plurality of the sub-CT images of the CT image. The reference physiological phase of each sub-CT image may be determined from the plurality of physiological phases based on the plurality of sub-gated PET images of the plurality of gated PET images.

For example, for a specific sub-CT image, the data processing system 130 may select, from the plurality of sub-gated PET images of the plurality of gated PET images, a plurality of candidate sub-gated PET images that correspond to the same portion of the subject as the specific sub-CT image. For each of the plurality of candidate sub-gated PET images, the data processing system 130 may determine a similarity degree between the specific sub-CT image and the candidate sub-gated PET image. The data processing system 130 may determine, among the plurality of candidate sub-gated PET images, a reference sub-gated PET image that has the highest similarity degree to the specific sub-CT image. The data processing system 130 may designate the physiological phase of the reference sub-gated PET image as the reference physiological phase of the specific sub-CT image. Merely by way of example, for a sub-CT image corresponding to the kidney of the subject, a plurality of sub-gated PET images corresponding to the kidney of the subject may be selected as the candidate sub-gated PET images. The physiological phase of a candidate sub-gated PET image that has the highest similarity degree with respect to the sub-CT image corresponding to the kidney may be designated as the reference physiological phase of the sub-CT image.

In some embodiments, the similarity degree between a sub-CT image and a candidate sub-gated PET image may include a pixel-based similarity, an entropy-based similarity, a mutual information similarity, or the like, or any combination thereof. The similarity degree may be determined based on the entire sub-CT image and the entire candidate sub-gated PET image. Alternatively, the similarity degree may be determined based on one or more sub-regions of the sub-CT image and corresponding portion(s) in the candidate sub-gated PET image. In some embodiments, a first VOI may be segmented from the candidate sub-gated PET image and a second VOI may be segmented from the sub-CT image based on an image segmentation technique. For example, the first VOI and the second VOI may be segmented by performing the process 900 on the candidate sub-gated PET image and the sub-CT image, respectively. The similarity degree between the sub-CT image and the candidate sub-gated PET image may be determined based on the first VOI and the second VOI.

In some embodiments, the first VOI and the second VOI may correspond to a specific portion of the subject that is affected by the physiological motion of the subject. The specific portion may satisfy one or more conditions. An exemplary condition may include that the specific portion is an internal portion of the subject. Another exemplary condition may include that a difference between VOIs corresponding to the specific portion in different gated PET images is greater than a first threshold. The difference between two VOIs may be measured by a pixel difference (e.g., a difference between average pixel values of the two VOIs), an area difference, or the like, or any combination thereof. Yet another exemplary condition may include that in the CT image, the variation of the voxel values corresponding to the specific portion along the axial direction of the subject exceeds a second threshold.

After the reference respiratory phase of each sub-CT image is determined, the data processing system 130 may determine a motion vector field between the target physiological phase and the reference physiological phase of the sub-CT image. Based on the motion vector field corresponding to each of the plurality of sub-CT images, the data processing system 130 may further determine the target motion vector field between the target physiological phase and the physiological phase of the CT image. The target motion vector field may be a hybrid motion vector field including the motion vector field corresponding to each of the sub-CT images.

In some embodiments, the target physiological phase may be any physiological phase among the physiological phases. For example, the target physiological phase may be a default setting of the imaging system 100. As another example, the target physiological phase may be selected from the physiological phases by a user or the data processing system 130 according to an actual need. In some embodiments, the physiological phases may include respiratory phases, and the target physiological phase may be an end-inspiration phase or an end-expiration phase. In some embodiments, the data processing system 130 may determine the motion vector field between the target physiological phase and the reference physiological phase of a sub-CT image by registering a gated PET image corresponding to the target physiological phase with a gated PET image corresponding to the reference physiological phase of the sub-CT image. More descriptions regarding the determination of a motion vector field between two physiological phases may be found elsewhere in the present disclosure, for example, operation 612 in FIG. 6 of the present disclosure. In some embodiments, the motion vector field between the target physiological phase and each of other physiological phase(s) may be previously determined. For example, the target physiological phase may be the end-inspiration phase, and the motion vector field between the end-inspiration phase and each of other respiratory phase(s) may be determined in operation 1302.

In 1308, the data processing system 130 (e.g., the reconstruction unit 520) may reconstruct an attenuation corrected PET image corresponding to the target physiological phase based on the target motion vector field, the CT image, and PET data used for the plurality of gated PET images reconstruction.

In some embodiments, the data processing system 130 may determine a physiological phase-matched CT image for the target physiological phase by transforming the CT image based on the target motion vector field between the target physiological phase and the physiological phase of the CT image. The data processing system 130 may further reconstruct the attenuation corrected PET image corresponding to the target physiological phase based on the physiological phase-matched CT image and the gated PET image (or gated PET data) corresponding to the target physiological phase.

For example, in the transformation of the CT image, each sub-CT image may be transformed based on the motion vector field between the target physiological phase and the reference physiological phase of the sub-CT image. The transformed CT image may have a plurality of transformed sub-CT images, each of which may have a matched physiological phase (e.g., a matched respiratory phase) with the gated PET image corresponding to the target physiological phase (or referred to as a target gated PET image). Thus, the transformed CT image may also be referred to as the physiological phase-matched CT image corresponding to the target gated PET image. In some embodiments, the reconstruction of the attenuation corrected PET image corresponding to the target physiological phase may be performed in a similar manner as that of an attenuation corrected PET image corresponding to a target respiratory phase as described in connection with operations 614-618, and the descriptions thereof are not repeated here.

It should be noted that the above descriptions of the process 1300 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted, and/or one or more additional operations may be added. For example, operation 1302 and operation 1304 may be combined into a single operation. As another example, the process 1300 may include an additional operation for dividing the CT image into the plurality of sub-CT images, and an additional operation for dividing the each of the plurality of gated PET images into the plurality of sub-gated PET images.

EXAMPLES

The following examples are provided for illustration purposes and not intended to limit the scope of the present disclosure.

Figure 10A:
FIGS. 10A to 10C illustrate exemplary sub-regions in a CT image according to some embodiments of the present disclosure.
Figure 10B:
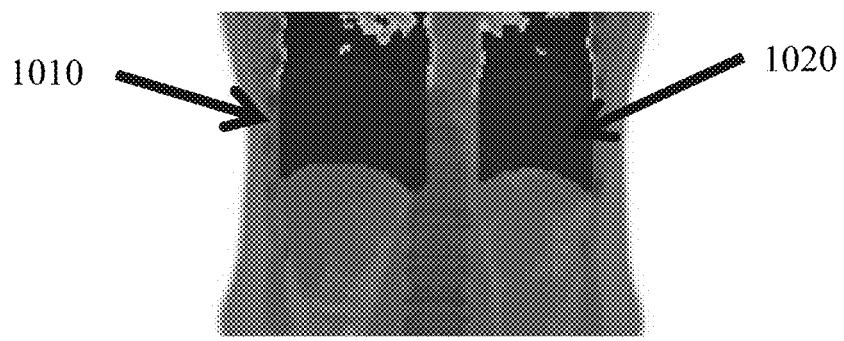
Figure 10C:
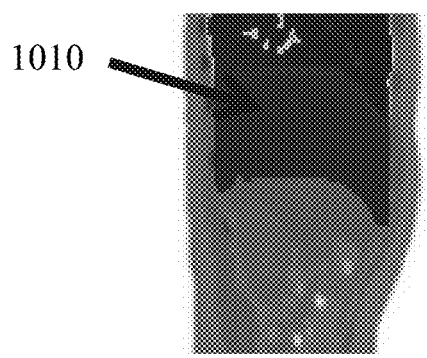

FIGS. 10A to 10C illustrate exemplary sub-regions 1010 and 1020 in a CT image according to some embodiments of the present disclosure. FIGS. 10A to 10C illustrate a transverse plane, a coronal plane, and a sagittal plane of the sub-regions 1010 and 1020, respectively. The second sub-region 1010 includes a right lung and the first sub-region 1020 includes a left lung. After portions corresponding to the right lung and the left lung were segmented in the CT image, the portions were extended downward toward the liver and the stomach to obtain the sub-regions 1010 and 1020. The sub-regions 1010 and 1020 include a portion of the liver and a portion of the stomach of the subject. In some embodiments, the sub-regions 1010 and 1020 may be used in the determination of a reference respiratory phase of the CT image.

Figure 11A:
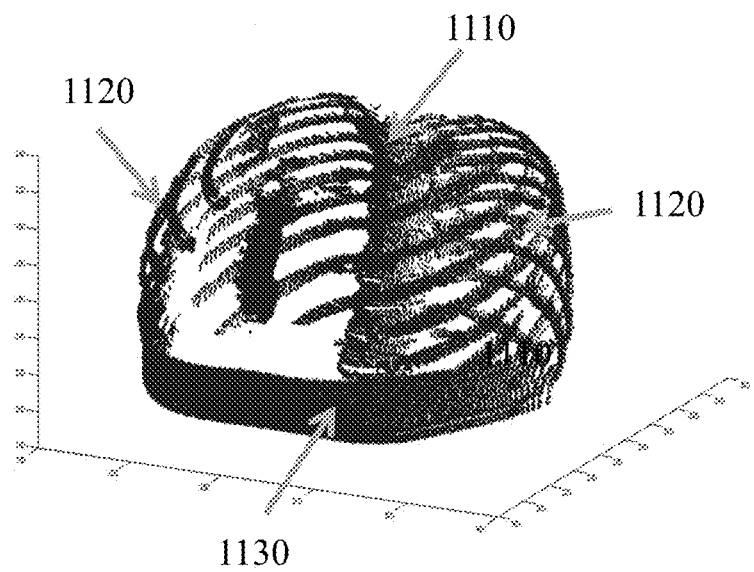
FIGS. 11A and 11B illustrate exemplary edge points of bones within a thoracic and abdominal cavity of a subject according to some embodiments of the present disclosure.
Figure 11B:
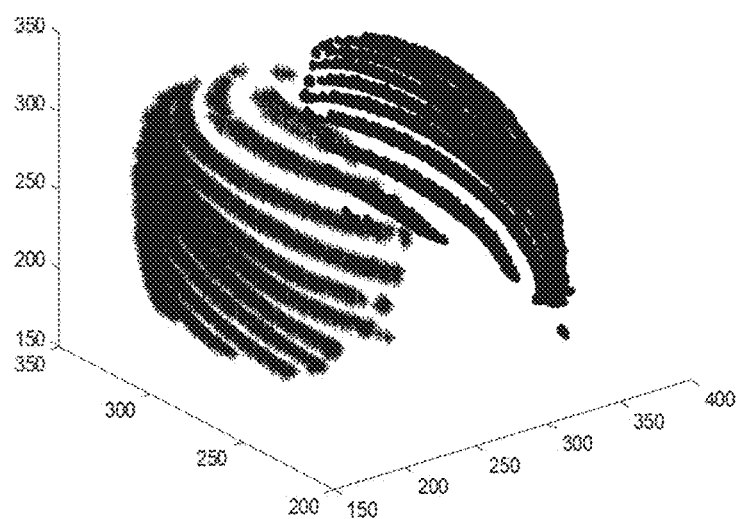

FIGS. 11A and 11B illustrate exemplary edge points of bones surrounding the thoracic and cavity of a subject according to some embodiments of the present disclosure. The bones surrounding the thoracic and abdominal cavity include ribs 1120 and the spine 1110 of the imaged subject. FIG. 11A illustrates edge points of bones on the back of the subject and edge points of bones in the front portion of the abdominal cavity. The bones on the back of the subject include the spine 1110 and the ribs 1120.

The subject has no or few bones in the front portion of the abdomen. The edge points of the front portion of the abdomen are determined based on the body surface of the subject in the front portion of the abdomen. The edge points 1130 in the front portion of the abdomen illustrated in FIG. 11A were determined to be points located at a predetermined distance away from the body surface of the subject in front of the abdomen. FIG. 11B illustrates edge points of the left ribs and the right ribs of the subject.

Figure 11C:
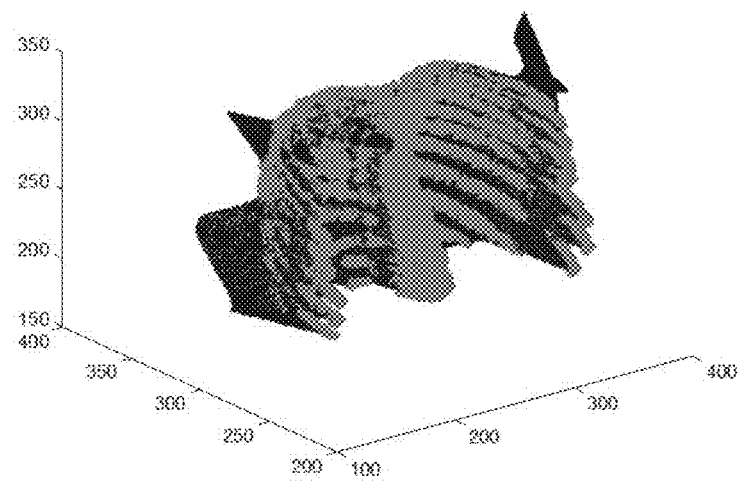
FIG. 11C illustrates an exemplary rear surface of a thoracic and abdominal cavity according to some embodiments of the present disclosure.
Figure 11D:
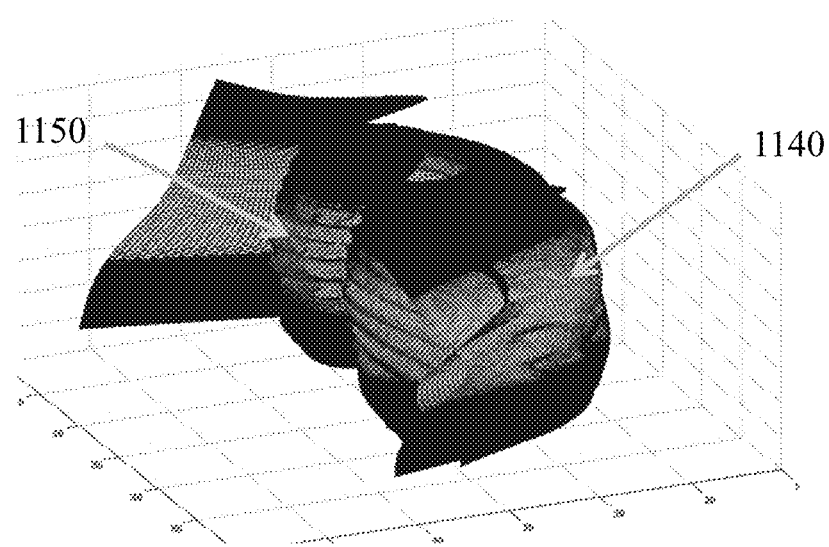
FIG. 11D illustrates exemplary a front surface and a rear surface of a thoracic and abdominal cavity according to some embodiments of the present disclosure.
Figure 11E:
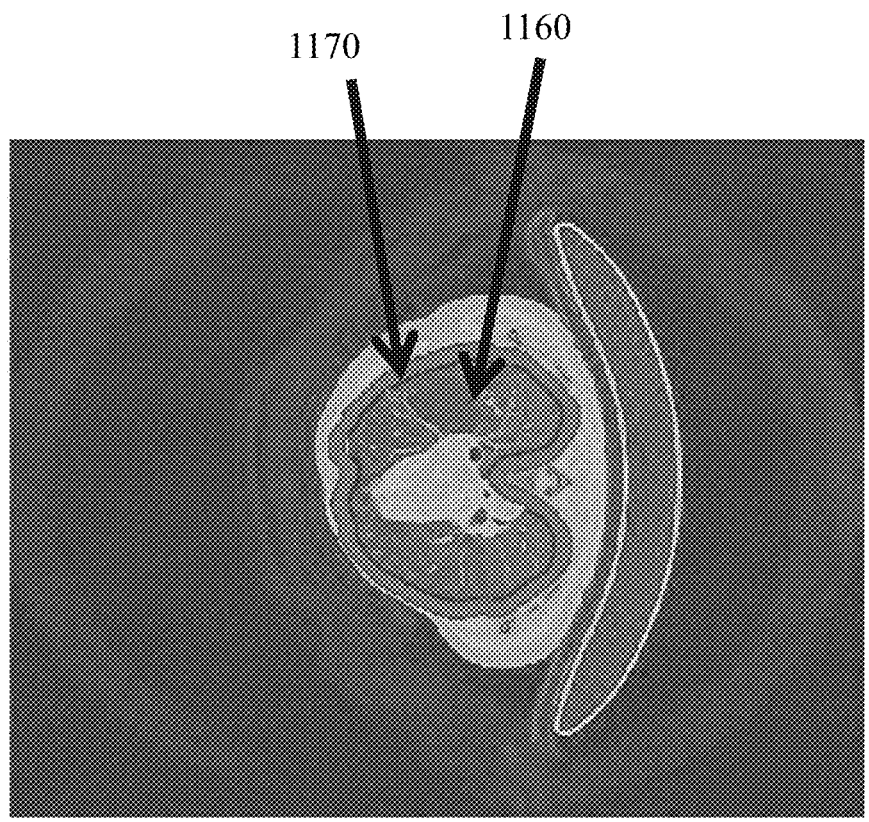
FIG. 11E illustrates a transversal plane of a boundary of an exemplary VOI in a CT image according to some embodiments of the present disclosure.

As described in connection with FIG. 9, one or more surfaces of the thoracic and abdominal cavity in a CT image may be determined based on the edge points. The one or more surfaces may include a front surface, a rear surface, a left surface, and a right surface. A VOI enclosed by the surfaces may be designated as a VOI in the CT image. FIG. 11C illustrates an exemplary rear surface of the thoracic and abdominal cavity of a subject that was determined according to some embodiments of the present disclosure. FIG. 11D illustrates a front surface 1140 and a rear surface 1150 of the thoracic and abdominal cavity of the subject that were determined according to some embodiments of the present disclosure. FIG. 11E illustrates a transversal plane of the boundary of an exemplary VOI 1160 in a CT image that was determined according to some embodiments of the present disclosure. The VOI 1170 may be enclosed by a closed curve 1170. The closed curve 1170 was determined by combining the front surface, the rear surface, the left surface, and the right surface of the thoracic and abdominal cavity of the subject.

Figure 12A:
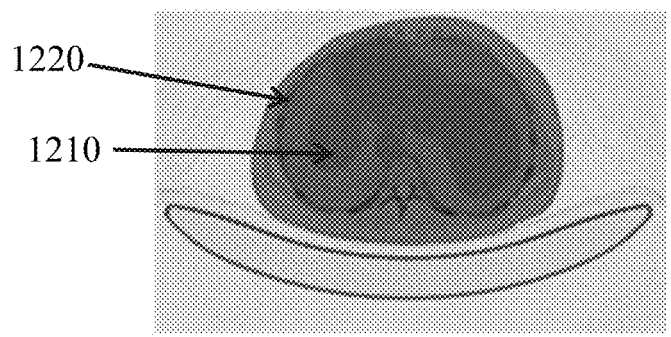
FIGS. 12A to 12C illustrate an exemplary VOI in a CT image according to some embodiments of the present disclosure.
Figure 12B:
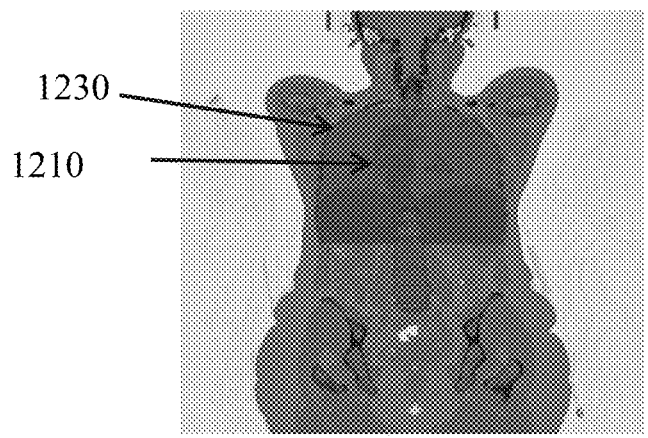
Figure 12C:
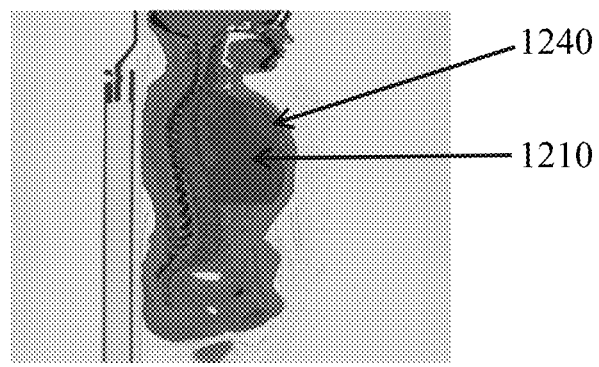

FIGS. 12A to 12C illustrate an exemplary VOI 1210 in a CT image that was determined according to some embodiments of the present disclosure. FIGS. 12A to 12C illustrate a transverse plane, a coronal plane, and a sagittal plane of the VOI 1210 in the CT image, respectively. The VOI 1210 on the transverse plane is enclosed by a closed curve 1220. The VOI 1210 on the coronal plane is enclosed by a closed curve 1230. The VOI 1210 on the sagittal plane is enclosed by a closed curve 1240. In some embodiments, the VOI 1210 may be a VOI within a thoracic and abdominal cavity that excludes one or more bones of a subject.

Figure 14A:
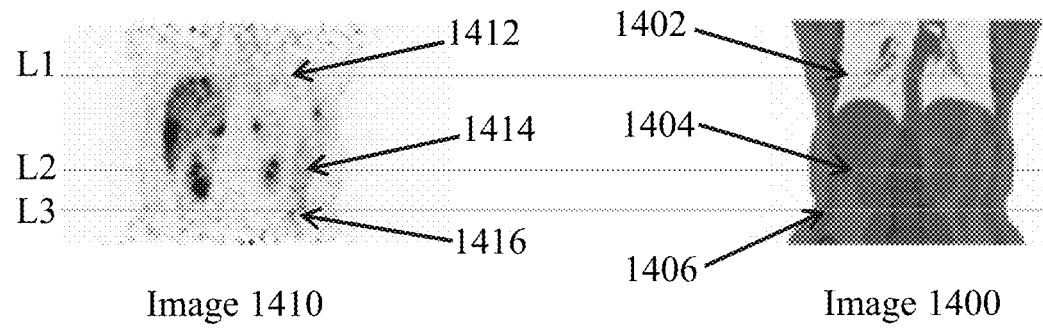
FIG. 14A illustrates an exemplary matching result between a CT image and a gated PET image corresponding to an end-expiration phase according to some embodiments of the present disclosure.
Figure 14B:
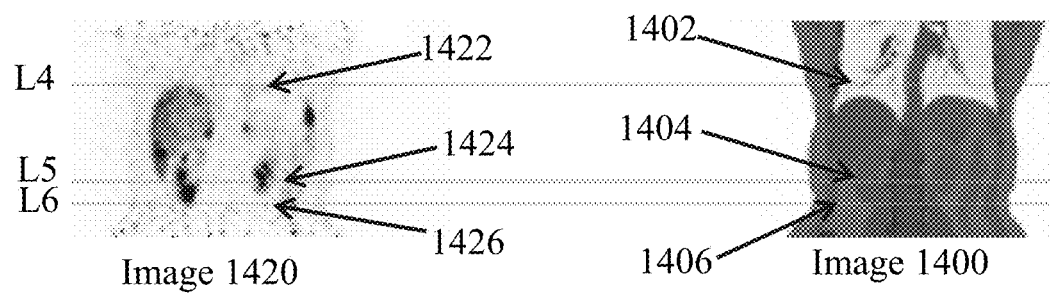
FIG. 14B illustrates an exemplary matching result between a CT image and a gated PET image corresponding to an end-inspiration phase according to some embodiments of the present disclosure.

FIG. 14A illustrates an exemplary matching result between a CT image 1400 and a gated PET image 1410 corresponding to an end-expiration phase according to some embodiments of the present disclosure. FIG. 14B illustrates an exemplary matching result between the CT image 1400 and a gated PET image 1420 corresponding to an end-inspiration phase according to some embodiments of the present disclosure.

The CT image 1400 was acquired by a spiral CT device when a patient is inhaling deeply and corresponds to a hybrid respiratory phase including a deep inspiration phase. The CT image 1400 includes CT slice images 1402, 1404, and 1406 corresponding to different respiratory phases as shown in FIG. 14A.

The gated PET image 1410 includes PET slice images 1412, 1414, and 1416 each of which corresponds to the end-expiration phase. According to FIG. 14A, the CT slice image 1404 corresponds to the same (or substantially the same) slice of the patient as the PET slice image 1414 (denoted by line L2). However, the CT slice image 1402 corresponds to a slice of the patient different from the PET slice image 1412 (denoted by line L1), and the CT slice image 1406 corresponds to a slice of the patient different from the PET slice image 1416 (denoted by line L3). Overall, the gated PET image 1410 corresponding to the end-expiration phase mismatches the CT image 1400, which may cause artifacts if an attenuation corrected PET image is reconstructed based on the CT image 1400 and the gated PET image 1410.

As illustrated in FIG. 14B, the gated PET image 1420 includes PET slice images 1422, 1424, and 1426 each of which corresponds to the end-inspiration phase. According to FIG. 14B, the CT slice image 1404 correspond to the same (or substantially the same) slice of the patient as the PET slice image 1424 (denoted by line L5), and the CT slice image 1406 corresponds to the same (or substantially the same) slice of the patient as the PET slice image 1426 (denoted by line L6). However, the CT slice image 1402 corresponds to a slice of the patient different from the PET slice image 1432 (denoted by line L4). Overall, the gated PET image 1420 corresponding to the end-inspiration phase mismatches the CT image 1400, which may cause artifacts if an attenuation corrected PET image is reconstructed based on the CT image 1400 and the gated PET image 1420.

Figure 14C:
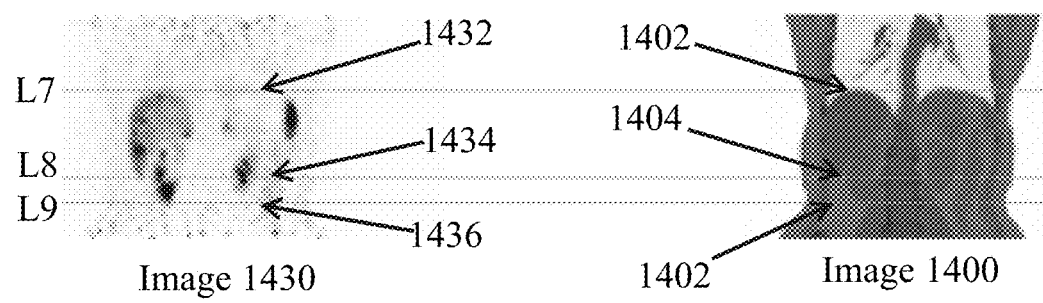
FIG. 14C illustrates an exemplary matching result between a CT image and a transformed gated PET image according to some embodiments of the present disclosure.

FIG. 14C illustrates an exemplary matching result of the CT image 1400 and a transformed gated PET image 1430 according to some embodiments of the present disclosure.

The transformed gated PET image 1430 was generated by transforming the gated PET image 1420 based on a target motion vector field between the end-inspiration phase and a respiratory phase of the CT image. The target motion vector field was determined by performing operations 1302-1306 as described in connection with FIG. 13. The corrected gated PET image 1430 includes PET slice images 1432, 1434, and 1436 corresponding to different respiratory phases. As shown in FIG. 14C, the CT slice image 1402 corresponds to the same slice of the patient as the PET slice image 1432 (denoted by line L7), the CT slice image 1404 corresponds to the same slice of the patient as the PET slice image 1434 (denoted by line L8), and the CT slice image 1406 corresponds to the same slice of the patient as the PET slice image 1436 (denoted by line L9). This indicates that the transformed gated PET image 1430 matches the CT image 1400.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "module," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for image processing, comprising:
at least one storage device including a set of instructions; and
at least one processor configured to communicate with the at least one storage device, wherein when executing the set of instructions, the at least one processor is configured to direct the system to perform operations including:
obtaining a plurality of gated positron emission tomography (PET) images of a subject, each of the plurality of gated PET images corresponding to one physiological phase of a plurality of physiological phases of the subject, each of the plurality of gated PET images including a plurality of sub-gated PET images each of which corresponds to one of a plurality of portions of the subject;
obtaining a computed tomography (CT) image of the subject, the CT image being acquired by performing a spiral CT scan on the subject and including a plurality of sub-CT images each of which corresponds to one of the plurality of portions of the subject;
determining a target motion vector field between a target physiological phase among the plurality of physiological phases and a physiological phase of the CT image based on the plurality of sub-gated PET images and the plurality of sub-CT images; and
reconstructing an attenuation corrected PET image corresponding to the target physiological phase based on the target motion vector field, the CT image, and PET data used for the plurality of gated PET images reconstruction.

2. The system of claim 1, wherein the determining a target motion vector field between a target physiological phase among the plurality of physiological phases and a physiological phase of the CT image based on the plurality of sub-gated PET images and the plurality of sub-CT images comprises:
for each of the plurality of sub-CT images,
determining, among the plurality of physiological phases, a reference physiological phase of the sub-CT image based on the plurality of sub-gated PET images of the plurality of gated PET images; and
determining a motion vector field between the target physiological phase and the reference physiological phase of the sub-CT image; and
determining, based on the motion vector field corresponding to each of the plurality of sub-CT images, the target motion vector field between the target physiological phase and the physiological phase of the CT image, the physiological phase of the CT image including the reference physiological phase of each of the plurality of sub-CT images.

3. The system of claim 2, wherein for each of the plurality of sub-CT images, the determining, among the plurality of physiological phases, a reference physiological phase of the sub-CT image based on the plurality of sub-gated PET images of the plurality of gated PET images comprises:
selecting, from the plurality of sub-gated PET images of the plurality of gated PET images, a plurality of candidate sub-gated PET images that correspond to the same portion of the subject as the sub-CT image;
for each of the plurality of candidate sub-gated PET images, determining a similarity degree between the sub-CT image and the candidate sub-gated PET image;
determining, among the plurality of candidate sub-gated PET images, a reference sub-gated PET image that has the highest similarity degree to the sub-CT image; and
designating the physiological phase of the reference sub-gated PET image as the reference physiological phase of the sub-CT image.

4. The system of claim 3, wherein for each of the plurality of candidate sub-gated PET images, the determining a similarity degree between the sub-CT image and the candidate sub-gated PET image comprises:
segmenting a first volume of interest (VOI) from the candidate sub-gated PET image;
segmenting a second VOI from the sub-CT image; and
determining, based on the first VOI and the second VOI, the similarity degree between the sub-CT image and the candidate sub-gated PET image.

5. The system of claim 1, wherein the at least one processor is further configured to direct the system to perform the operations including:
dividing the CT image into the plurality of sub-CT images each of which corresponds to one of the plurality of portions of the subject; and
for each of the plurality of gated PET images, dividing the gated PET image into the plurality of sub-gated PET images each of which corresponds to one of the plurality of portions of the subject.

6. The system of claim 1, wherein the target physiological phase is an end-inspiration phase.

7. The system of claim 1, wherein the plurality of physiological phases are respiratory phases, and the plurality of respiratory phases comprise an end-expiration phase, an end-inspiration phase, a deep expiration phase, a deep inspiration phase, and one or more middle respiratory phases between the end-expiration phase and the end-inspiration phase.

8. The system of claim 7, wherein the obtaining a plurality of gated PET images of a subject comprises:
obtaining a first gated PET image corresponding to the end-inspiration phase and a second gated PET image corresponding to the end-expiration phase;
determining, based on the first gated PET image and the second gated PET image, a first motion vector field between the end-inspiration phase and the end-expiration phase; and
for each of the plurality of respiratory phases other than the end-inspiration phase and the end-expiration phase,
determining, based on the first motion vector field, a second motion vector field between the end-inspiration phase and the respiratory phase; and
generating, based on the second motion vector field and the first gated PET image, the gated PET image corresponding to the respiratory phase.

9. The system of claim 7, wherein the obtaining a plurality of gated PET images of a subject comprises:
obtaining PET data of the subject acquired when the subject is in a breathing status;
reconstructing, based on the PET data, a first gated PET image corresponding to the end-inspiration phase, a second gated PET image corresponding to the end-expiration phase, and one or more gated PET images corresponding to the one or more middle respiratory phases; and generating, based on the first gated PET image and the second gated PET image, a gated PET image corresponding to the deep expiration phase and a gated PET image corresponding to the deep inspiration phase.

10. The system of claim 1, wherein the at least one processor is further configured to direct the system to perform the operations including:

dividing the subject into the plurality of portions along a direction perpendicular to an axial plane of the subject.

11. A method for image processing, comprising:

obtaining a plurality of gated positron emission tomography (PET) images of a subject, each of the plurality of gated PET images corresponding to one physiological phase of a plurality of physiological phases of the subject, each of the plurality of gated PET images including a plurality of sub-gated PET images each of which corresponds to one of a plurality of portions of the subject;

obtaining a computed tomography (CT) image of the subject, the CT image being acquired by performing a spiral CT scan on the subject and including a plurality of sub-CT images each of which corresponds to one of the plurality of portions of the subject;

determining a target motion vector field between a target physiological phase among the plurality of physiological phases and a physiological phase of the CT image based on the plurality of sub-gated PET images and the plurality of sub-CT images; and reconstructing an attenuation corrected PET image corresponding to the target physiological phase based on the target motion vector field, the CT image, and PET data used for the plurality of gated PET images reconstruction.

12. The method of claim 11, wherein the determining a target motion vector field between a target physiological phase among the plurality of physiological phases and a physiological phase of the CT image based on the plurality of sub-gated PET images and the plurality of sub-CT images comprises:

for each of the plurality of sub-CT images,
determining, among the plurality of physiological phases, a reference physiological phase of the sub-CT image based on the plurality of sub-gated PET images of the plurality of gated PET images; and
determining a motion vector field between the target physiological phase and the reference physiological phase of the sub-CT image; and determining, based on the motion vector field corresponding to each of the plurality of sub-CT images, the target motion vector field between the target physiological phase and the physiological phase of the CT image, the physiological phase of the CT image including the reference physiological phase of each of the plurality of sub-CT images.

13. The method of claim 12, wherein for each of the plurality of sub-CT images, the determining, among the plurality of physiological phases, a reference physiological phase of the sub-CT image based on the plurality of sub-gated PET images of the plurality of gated PET images comprises:

selecting, from the plurality of sub-gated PET images of the plurality of gated PET images, a plurality of candidate sub-gated PET images that correspond to the same portion of the subject as the sub-CT image;

for each of the plurality of candidate sub-gated PET images, determining a similarity degree between the sub-CT image and the candidate sub-gated PET image;

determining, among the plurality of candidate sub-gated PET images, a reference sub-gated PET image that has the highest similarity degree to the sub-CT image; and designating the physiological phase of the reference sub-gated PET image as the reference physiological phase of the sub-CT image.

14. The method of claim 13, wherein for each of the plurality of candidate sub-gated PET images, the determining a similarity degree between the sub-CT image and the candidate sub-gated PET image comprises:

segmenting a first volume of interest (VOI) from the candidate sub-gated PET image;
segmenting a second VOI from the sub-CT image; and
determining, based on the first VOI and the second VOI, the similarity degree between the sub-CT image and the candidate sub-gated PET image.

15. The method of claim 11, wherein the target physiological phase is an end-inspiration phase.

16. The method of claim 11, wherein the plurality of physiological phases are respiratory phases, and the plurality of respiratory phases comprise an end-expiration phase, an end-inspiration phase, a deep expiration phase, a deep inspiration phase, and one or more middle respiratory phases between the end-expiration phase and the end-inspiration phase.

17. The method of claim 16, wherein the obtaining a plurality of gated PET images of a subject comprises:

obtaining a first gated PET image corresponding to the end-inspiration phase and a second gated PET image corresponding to the end-expiration phase;

determining, based on the first gated PET image and the second gated PET image, a first motion vector field between the end-inspiration phase and the end-expiration phase; and for each of the plurality of respiratory phases other than the end-inspiration phase and the end-expiration phase, determining, based on the first motion vector field, a second motion vector field between the end-inspiration phase and the respiratory phase; and generating, based on the second motion vector field and the first gated PET image, the gated PET image corresponding to the respiratory phase.

18. The method of claim 16, wherein the obtaining a plurality of gated PET images of a subject comprises:

obtaining PET data of the subject acquired when the subject is in a breathing status;

reconstructing, based on the PET data, a first gated PET image corresponding to the end-inspiration phase, a second gated PET image corresponding to the end-expiration phase, and one or more gated PET images corresponding to the one or more middle respiratory phases; and generating, based on the first gated PET image and the second gated PET image, a gated PET image corresponding to the deep expiration phase and a gated PET image corresponding to the deep inspiration phase.

19. The method of claim 11, further comprising:

dividing the subject into the plurality of portions along a direction perpendicular to an axial plane of the subject.

20. A non-transitory computer-readable storage medium storing instructions that, when executed by at least one processor of a system, cause the system to perform a method, the method comprising:

obtaining a plurality of gated positron emission tomography (PET) images of a subject, each of the plurality of gated PET images corresponding to one physiological phase of a plurality of physiological phases of the subject, each of the plurality of gated PET images including a plurality of sub-gated PET images each of which corresponds to one of a plurality of portions of the subject;

obtaining a computed tomography (CT) image of the subject, the CT image being acquired by performing a spiral CT scan on the subject and including a plurality of sub-CT images each of which corresponds to one of the plurality of portions of the subject;

determining a target motion vector field between a target physiological phase among the plurality of physiological phases and a physiological phase of the CT image based on the plurality of sub-gated PET images and the plurality of sub-CT images; and reconstructing an attenuation corrected PET image corresponding to the target physiological phase based on the target motion vector field, the CT image, and PET data used for the plurality of gated PET images reconstruction.

\* \* \* \* \*